US012577278B2

(12) United States Patent
Fu et al.

(10) Patent No.: US 12,577,278 B2
(45) Date of Patent: Mar. 17, 2026

(54) KRAS G12V MUTANT BINDS TO JAK1, INHIBITORS, PHARMACEUTICAL COMPOSITIONS, AND METHODS RELATED THERETO

(71) Applicant: Emory University, Atlanta, GA (US)

(72) Inventors: Haian Fu, Decatur, GA (US); Xiulei Mo, Snellville, GA (US); Cong Tang, Decatur, GA (US)

(73) Assignee: Emory University, Atlanta, GA (US)

( * ) Notice: Subject to any disclaimer, the term of this patent is extended or adjusted under 35 U.S.C. 154(b) by 748 days.

(21) Appl. No.: 17/617,269

(22) PCT Filed: Jun. 8, 2020

(86) PCT No.: PCT/US2020/036607
§ 371 (c)(1),
(2) Date: Dec. 7, 2021

(87) PCT Pub. No.: WO2020/247914
PCT Pub. Date: Dec. 10, 2020

(65) Prior Publication Data
US 2022/0306688 A1     Sep. 29, 2022

Related U.S. Application Data

(60) Provisional application No. 62/858,472, filed on Jun. 7, 2019.

(51) Int. Cl.
| | |
|---|---|
| *C07K 7/00* | (2006.01) |
| *A61K 47/62* | (2017.01) |
| *C07K 7/02* | (2006.01) |
| *G01N 33/50* | (2006.01) |
| *A61K 38/00* | (2006.01) |

(52) U.S. Cl.
CPC ............... *C07K 7/02* (2013.01); *A61K 47/62* (2017.08); *G01N 33/5011* (2013.01); *A61K 38/00* (2013.01)

(58) Field of Classification Search
CPC .......... C07K 7/02; A61K 47/62; A61K 38/00; G01N 33/5011
See application file for complete search history.

(56) References Cited

U.S. PATENT DOCUMENTS

| | | |
|---|---|---|
| 9,687,491 B1 | 6/2017 | Rabizadeh |
| 2005/0208558 A1 | 9/2005 | Venter |
| 2015/0050274 A1 | 2/2015 | Elenitoba-Johnson |
| 2016/0272639 A1 | 9/2016 | Crew |
| 2017/0304421 A1 * | 10/2017 | Wang ............. A61K 39/464464 |

FOREIGN PATENT DOCUMENTS

| | | | | |
|---|---|---|---|---|
| WO | WO-03027295 A2 * | 4/2003 | ............ | C07K 14/47 |
| WO | 2011098673 | 8/2011 | | |
| WO | 2017181061 | 10/2017 | | |
| WO | 2017189906 | 11/2017 | | |
| WO | WO-2018144082 A1 * | 8/2018 | ......... | A61K 31/7088 |
| WO | 2020052575 | 3/2020 | | |

OTHER PUBLICATIONS

Sakamoto et al., K-Ras(G12D)-selective inhibitory peptides generated by random peptide T7 phage display technology, Biochemical and Biophysical Research Communications; 484: 605-611. (Year: 2017).*

Falk et al. , Effect of mutant variants of the KRAS gene on PD-L1 expression and on the immune microenvironment and association with clinical outcome in lung adenocarcinoma patients, Lung Cancer; 121: 70-75. (Year: 2018).*

Prior et al., The Frequency of Ras Mutations in Cancer, Cancer Res.;80: 2969-74. doi: 10.1158/0008-5472.CAN-19-3682 (Year: 2020).*

Koullouridi et al., Prognostic Value of KRAS Mutations in Colorectal Cancer Patients, cancers; 14: 3320. https://doi.org/10.3390/cancers14143320 (Year: 2022).*

Hunter JC, Manandhar A, Carrasco MA, Gurbani D, Gondi S, Westover KD. Biochemical and Structural Analysis of Common Cancer-Associated KRAS Mutations. Mol Cancer Res. Sep. 2015;13(9):1325-35. (Year: 2015).*

Stephen AG, Esposito D, Bagni RK, McCormick F. Dragging ras back in the ring. Cancer Cell. Mar. 17, 2014;25(3):272-81.). (Year: 2014).*

Pan T., Zhang Y., Zhou N., He X., Chen C., Liang L., Duan X., Lin Y., Wu K., Zhang H. A recombinant chimeric protein specifically induces mutant KRAS degradation and potently inhibits pancreatic tumor growth. Oncotarget. 2016; 7: 44299-44309 (Year: 2016).*

Canon et al. The clinical KRAS(G12C) inhibitor AMG 510 drives anti-tumour immunity, Nature, 2019, 575(7781):217-223.

Gao et al. PROTAC Technology: Opportunities and Challenges, ACS Med. Chem. Lett. 2020, 11, 237-240.

Li et al. The OncoPPi network of cancer-focused protein-protein interactions to inform biological insights and therapeutic strategies, Nat Commun, 2017, 8:14356.

Smith et al. Differential PROTAC substrate specificity dictated by orientation of recruited E3 ligase, Nat Commun, 2019, 10(1):131.

Zaretsky et al. Mutations Associated with Acquired Resistance to PD-1 Blockade in Melanoma, N Engl J Med. 2016, 375(9): 819-829.

Adderley et al. KRAS-mutant non-small cell lung cancer: Converging small molecules and immune checkpoint inhibition, EBioMedicine, 41 (2019) 711-716.

Khvalevsky et al. Mutant KRAS is a druggable target for pancreatic cancer, Proc Natl Acad Sci U S A, 2013, 110 (51):20723-8.

(Continued)

*Primary Examiner* — Fred H Reynolds
*Assistant Examiner* — Sara E Konopelski Snavely
(74) *Attorney, Agent, or Firm* — Emory University

(57) ABSTRACT

This disclosure relates to the discovery that a G12V mutant of KRAS (hereinafter KRAS G12V) binds to JAK1, i.e., the existence of a KRAS G12V and JAK1 binding interaction. In certain embodiments, this disclosure relates to methods of disrupting the KRAS G12V and JAK1 interaction reversing KRAS G12V induced immune escape by cancer cells utilizing agents that prevent the binding of JAK1 to KRAS G12V.

11 Claims, 7 Drawing Sheets

Specification includes a Sequence Listing.

(56) References Cited

OTHER PUBLICATIONS

Polom et al. KRAS Mutation in Gastric Cancer and Prognostication Associated with Microsatellite Instability Status, Pathol. Oncol. Res. (2019) 25:333-340.

Sideris et al. The Role of KRAS in Endometrial Cancer: A Mini-Review, Anticancer Research 39: 533-540 (2019).

Yang et al. KRAS Mutations in Solid Tumors: Characteristics, Current Therapeutic Strategy, and Potential Treatment Exploration, J. Clin. Med. 2023, 12, 709.

Zou et al. KRASG12D-mediated oncogenic transformation of thyroid follicular cells requires long-term TSH stimulation and is regulated by SPRY1, Laboratory Investigation (2015) 95, 1269-1277.

BD Transduction Laboratories TM Purified Mouse Anti-JAK1, (610231) Human JAK1 aa. 551-766, 2023.

Extended European Search Report, EP application No. 20818184.2, dated Mar. 22, 2023.

European Search Report, EP application No. 20818184.2, dated Nov. 21, 2023.

Lupardus et al. Structural Snapshots of Full-Length Jak1, a Transmembrane gp130/IL-6/IL-6R Cytokine Receptor Complex, and the Receptor-Jak1 Holocomplex, Structure, 2011, 19(1):45-55.

Roskoski et al. Janus kinase (JAK) inhibitors in the treatment of inflammatory and neoplastic diseases, Pharmacological Research 111 (2016) 784-803.

Singleton et al. Synthesis and biological evaluation of novel pyrazolo[l,5-a]pyrimidines: Discovery of a selective inhibitor of JAKI JH2 pseudokinase and VPS34, Bioorganic & Medicinal Chemistry Letters 30 (2020) 12681.

Tokarski et al. Tyrosine Kinase 2-mediated Signal Transduction in T Lymphocytes Is Blocked by Pharmacological Stabilization of Its Pseudokinase Domain, J Biol Chem, 2015, 290(17):11061-74.

UNIPROT, JAK human, No. P23458, 2019.

Wroblleski et al. Highly Selective Inhibition of Tyrosine Kinase 2 (TYK2) for the Treatment of Autoimmune Diseases: Discovery of the Allosteric Inhibitor BMS-986165, J. Med. Chem. 2019, 62, 8973-8995.

Zhu et al. Inhibition of KRAS-driven tumorigenicity by interruption of an autocrine cytokine circuit, Cancer Discov. 2014, 4(4): 452-465.

* cited by examiner

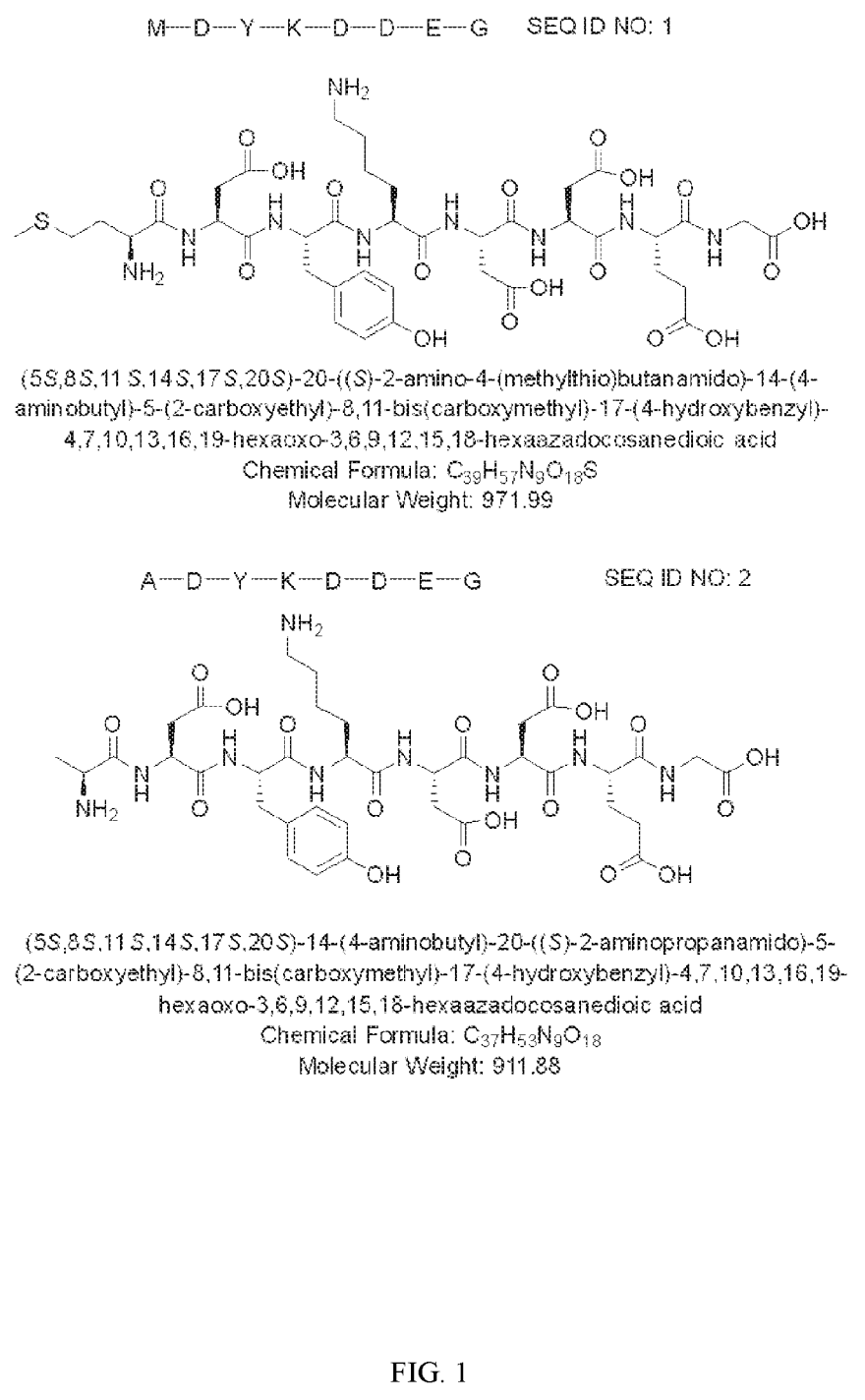

M——D——Y——K——D——D——E——G     SEQ ID NO: 1

(5S,8S,11S,14S,17S,20S)-20-((S)-2-amino-4-(methylthio)butanamido)-14-(4-aminobutyl)-5-(2-carboxyethyl)-8,11-bis(carboxymethyl)-17-(4-hydroxybenzyl)-4,7,10,13,16,19-hexaoxo-3,6,9,12,15,18-hexaazadocosanedioic acid
Chemical Formula: $C_{39}H_{57}N_9O_{18}S$
Molecular Weight: 971.99

A——D——Y——K——D——D——E——G          SEQ ID NO: 2

(5S,8S,11S,14S,17S,20S)-14-(4-aminobutyl)-20-((S)-2-aminopropanamido)-5-(2-carboxyethyl)-8,11-bis(carboxymethyl)-17-(4-hydroxybenzyl)-4,7,10,13,16,19-hexaoxo-3,6,9,12,15,18-hexaazadocosanedioic acid
Chemical Formula: $C_{37}H_{53}N_9O_{18}$
Molecular Weight: 911.88

FIG. 1

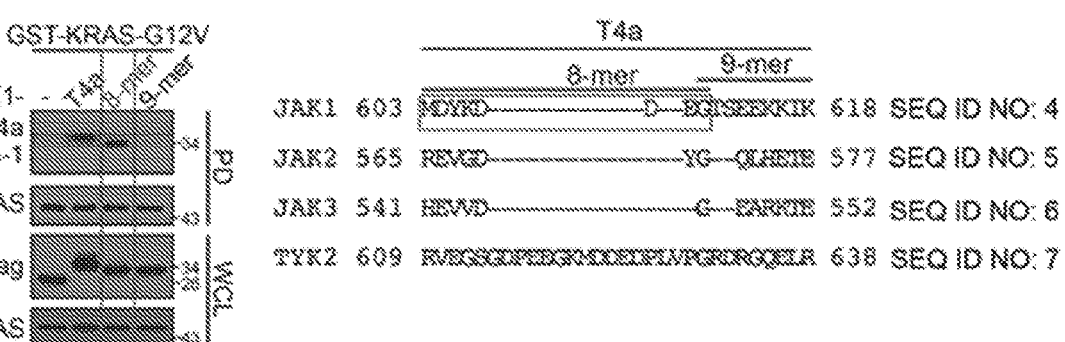
FIG. 2A
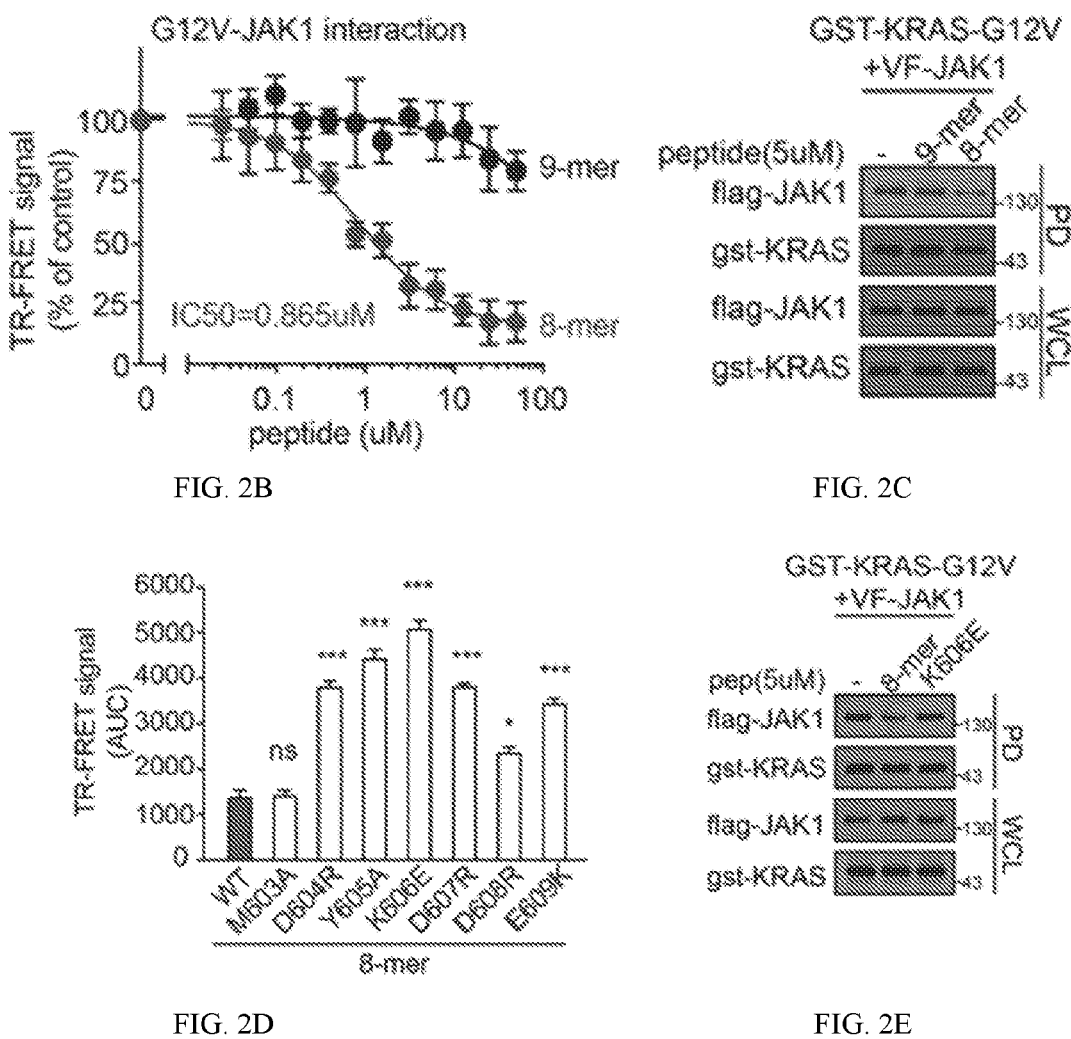
FIG. 2B                    FIG. 2C
FIG. 2D                    FIG. 2E

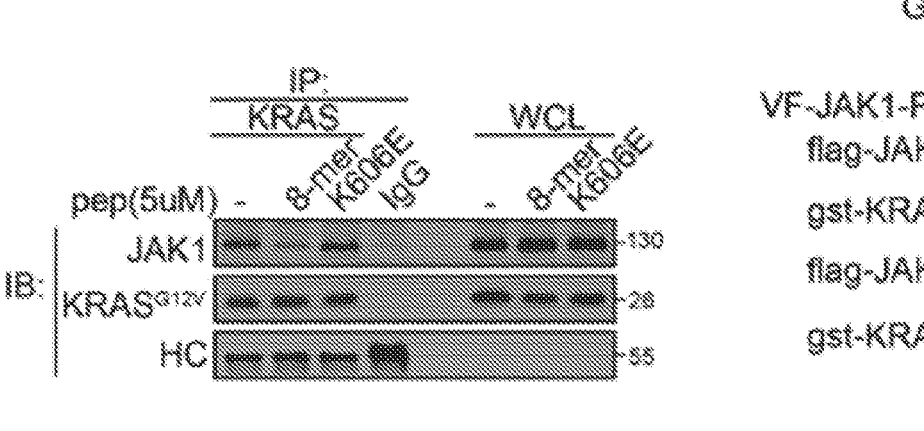
FIG. 2F                          FIG. 2G
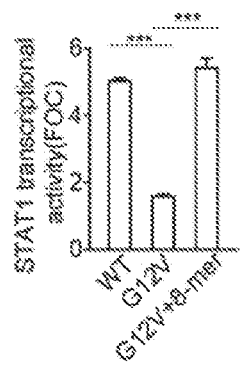
FIG. 3A
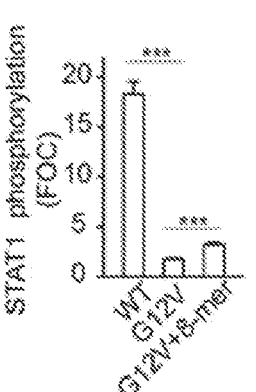 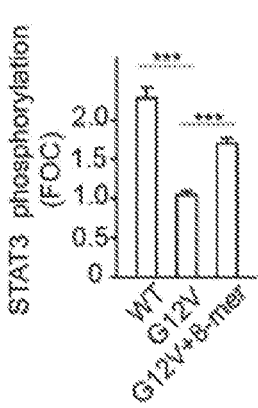 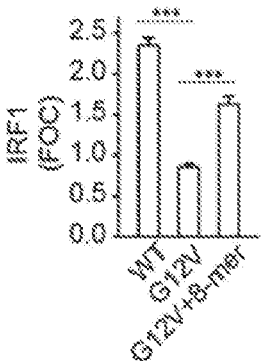 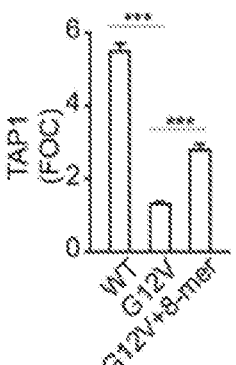
FIG. 3B

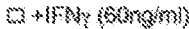
□ +IFNγ (60ng/ml)
▤ 8-mer(25nM)
■ IFNγ (60ng/ml)+8-mer(25nM)
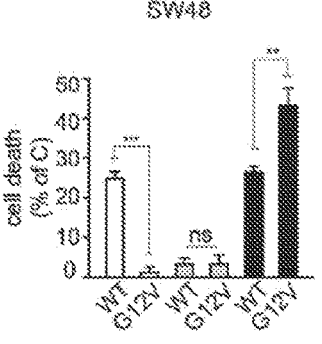
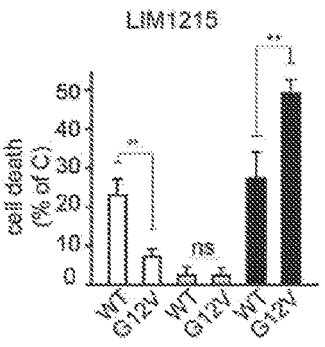
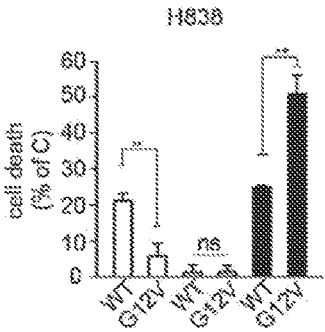
FIG. 4A
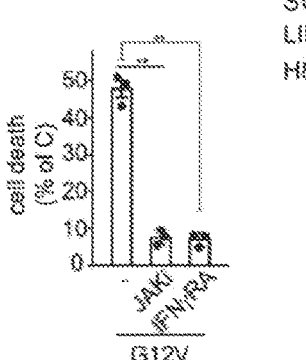
FIG. 4B
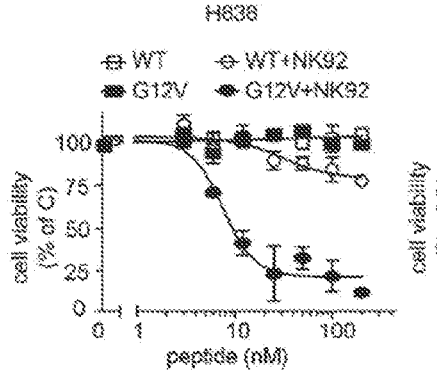
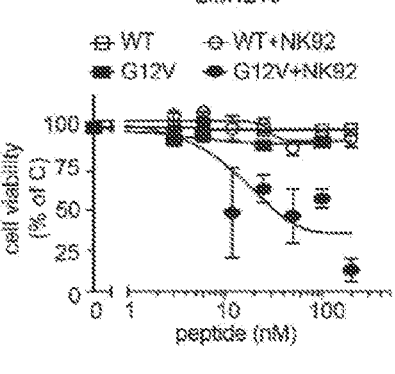
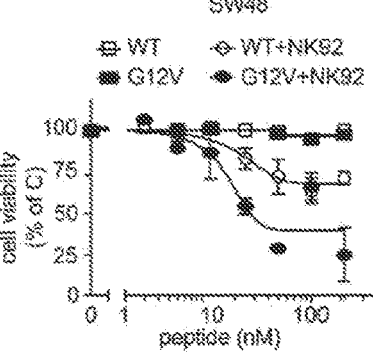
FIG. 4C

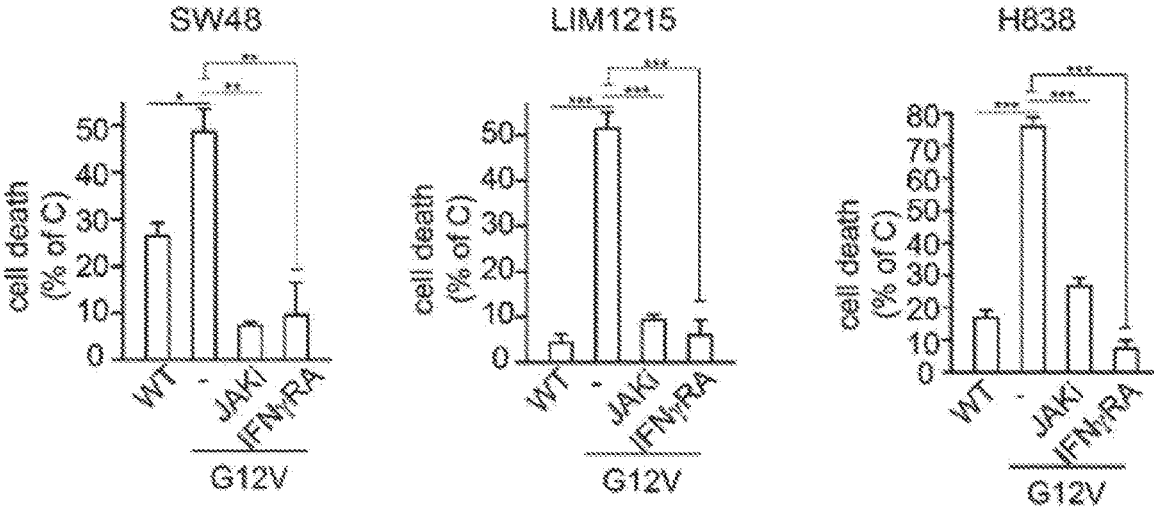
FIG. 4D
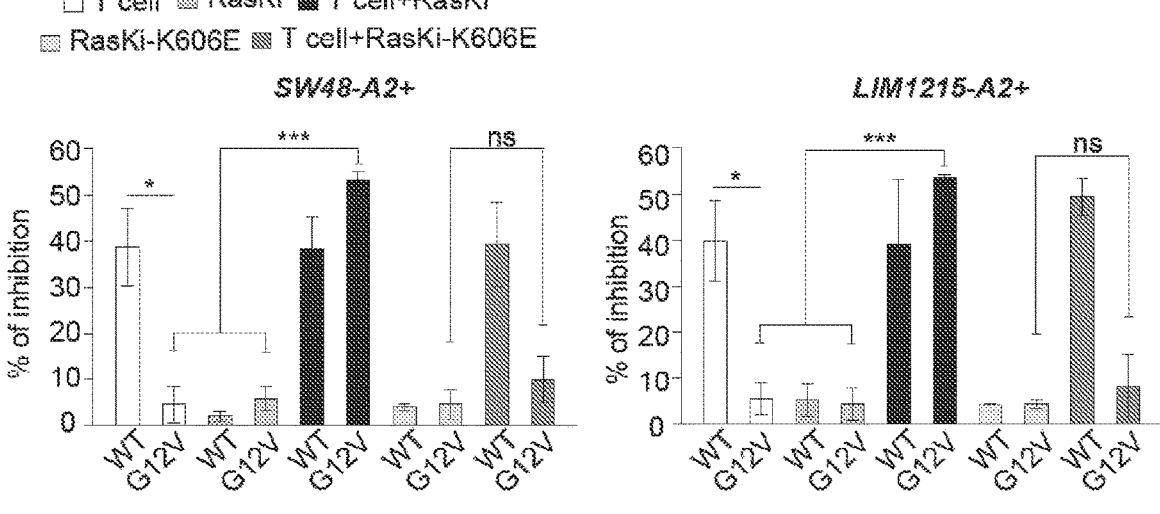
FIG. 5A                         FIG. 5B

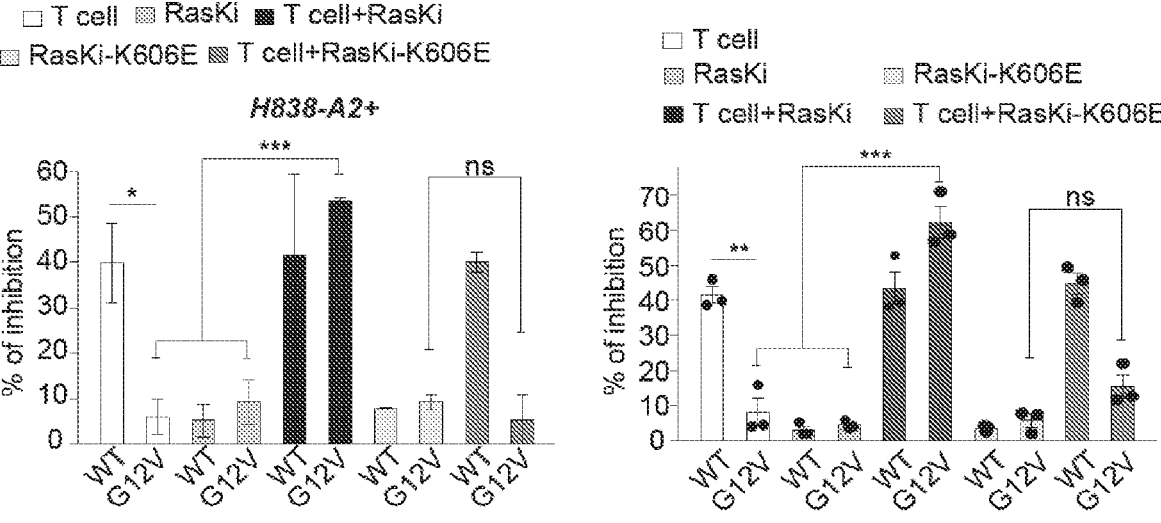
FIG. 5C                                          FIG. 5D
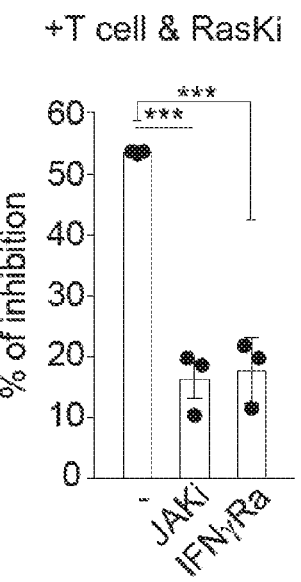
FIG. 5E
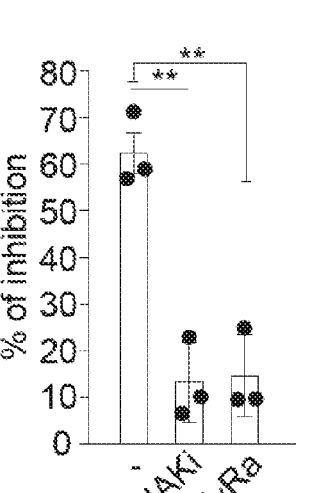
FIG. 5F

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial
<220> FEATURE:
<223> OTHER INFORMATION: Synthetic construct

<400> SEQUENCE: 1

Met Asp Tyr Lys Asp Asp Glu Gly
1               5

<210> SEQ ID NO 2
<211> LENGTH: 8
<212> TYPE: PRT
<213> ORGANISM: Artificial
<220> FEATURE:
<223> OTHER INFORMATION: Synthetic construct

<400> SEQUENCE: 2

Ala Asp Tyr Lys Asp Asp Glu Gly
```

-continued
_____

```
1               5

<210> SEQ ID NO 3
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Asp Tyr Lys Asp Asp Glu Gly
1               5

<210> SEQ ID NO 4
<211> LENGTH: 16
<212> TYPE: PRT
<213> ORGANISM: Artificial
<220> FEATURE:
<223> OTHER INFORMATION: Synthetic construct

<400> SEQUENCE: 4

Met Asp Tyr Lys Asp Asp Glu Gly Thr Ser Glu Glu Lys Lys Ile Lys
1               5                   10                  15

<210> SEQ ID NO 5
<211> LENGTH: 13
<212> TYPE: PRT
<213> ORGANISM: Artificial
<220> FEATURE:
<223> OTHER INFORMATION: Synthetic construct

<400> SEQUENCE: 5

Arg Glu Val Gly Asp Tyr Gly Gln Leu His Glu Thr Glu
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic construct

<400> SEQUENCE: 6

His Glu Val Val Asp Gly Glu Ala Arg Lys Thr Glu
1               5                   10

<210> SEQ ID NO 7
<211> LENGTH: 30
<212> TYPE: PRT
<213> ORGANISM: Artificial
<220> FEATURE:
<223> OTHER INFORMATION: Synthetic construct

<400> SEQUENCE: 7

Arg Val Glu Gly Ser Gly Asp Pro Glu Glu Asp Lys Met Asp Asp Glu
1               5                   10                  15

Asp Pro Leu Val Pro Gly Arg Asp Arg Gly Gln Glu Leu Arg
            20                  25                  30

<210> SEQ ID NO 8
<211> LENGTH: 25
<212> TYPE: PRT
<213> ORGANISM: Artificial
```

```
<220> FEATURE:
<223> OTHER INFORMATION: Synthetic construct

<400> SEQUENCE: 8

Met Asp Tyr Lys Asp Asp Glu Gly Thr Ser Glu Glu Lys Lys Ile Lys
1               5                   10                  15

Val Ile Leu Lys Val Leu Asp Pro Ser
            20                  25

<210> SEQ ID NO 9
<211> LENGTH: 83
<212> TYPE: PRT
<213> ORGANISM: Artificial
<220> FEATURE:
<223> OTHER INFORMATION: Synthetic construct

<400> SEQUENCE: 9

Gln Pro Lys Pro Arg Glu Ile Ser Asn Leu Leu Val Ala Thr Lys Lys
1               5                   10                  15

Ala Gln Glu Trp Gln Pro Val Tyr Pro Met Ser Gln Leu Ser Phe Asp
            20                  25                  30

Arg Ile Leu Lys Lys Asp Leu Val Gln Gly Glu His Leu Gly Arg Gly
        35                  40                  45

Thr Arg Thr His Ile Tyr Ser Gly Thr Leu Met Asp Tyr Lys Asp Asp
    50                  55                  60

Glu Gly Thr Ser Glu Glu Lys Lys Ile Lys Val Ile Leu Lys Val Leu
65                  70                  75                  80

Asp Pro Ser

<210> SEQ ID NO 10
<211> LENGTH: 128
<212> TYPE: PRT
<213> ORGANISM: Artificial
<220> FEATURE:
<223> OTHER INFORMATION: Synthetic construct

<400> SEQUENCE: 10

Gln Pro Lys Pro Arg Glu Ile Ser Asn Leu Leu Val Ala Thr Lys Lys
1               5                   10                  15

Ala Gln Glu Trp Gln Pro Val Tyr Pro Met Ser Gln Leu Ser Phe Asp
            20                  25                  30

Arg Ile Leu Lys Lys Asp Leu Val Gln Gly Glu His Leu Gly Arg Gly
        35                  40                  45

Thr Arg Thr His Ile Tyr Ser Gly Thr Leu Met Asp Tyr Lys Asp Asp
    50                  55                  60

Glu Gly Thr Ser Glu Glu Lys Lys Ile Lys Val Ile Leu Lys Val Leu
65                  70                  75                  80

Asp Pro Ser His Arg Asp Ile Ser Leu Ala Phe Phe Glu Ala Ala Ser
            85                  90                  95

Met Met Arg Gln Val Ser His Lys His Ile Val Tyr Leu Tyr Gly Val
            100                 105                 110

Cys Val Arg Asp Val Glu Asn Ile Met Val Glu Glu Phe Val Glu Gly
        115                 120                 125

<210> SEQ ID NO 11
<211> LENGTH: 311
<212> TYPE: PRT
<213> ORGANISM: Artificial
<220> FEATURE:
<223> OTHER INFORMATION: Synthetic construct
```

-continued

```
<400> SEQUENCE: 11

Gln Pro Lys Pro Arg Glu Ile Ser Asn Leu Leu Val Ala Thr Lys Lys
1               5                   10                  15

Ala Gln Glu Trp Gln Pro Val Tyr Pro Met Ser Gln Leu Ser Phe Asp
            20                  25                  30

Arg Ile Leu Lys Lys Asp Leu Val Gln Gly Glu His Leu Gly Arg Gly
        35                  40                  45

Thr Arg Thr His Ile Tyr Ser Gly Thr Leu Met Asp Tyr Lys Asp Asp
        50                  55                  60

Glu Gly Thr Ser Glu Glu Lys Lys Ile Lys Val Ile Leu Lys Val Leu
65                  70                  75                  80

Asp Pro Ser His Arg Asp Ile Ser Leu Ala Phe Phe Glu Ala Ala Ser
            85                  90                  95

Met Met Arg Gln Val Ser His Lys His Ile Val Tyr Leu Tyr Gly Val
            100                 105                 110

Cys Val Arg Asp Val Glu Asn Ile Met Val Glu Glu Phe Val Glu Gly
        115                 120                 125

Gly Pro Leu Asp Leu Phe Met His Arg Lys Ser Asp Val Leu Thr Thr
    130                 135                 140

Pro Trp Lys Phe Lys Val Ala Lys Gln Leu Ala Ser Ala Leu Ser Tyr
145                 150                 155                 160

Leu Glu Asp Lys Asp Leu Val His Gly Asn Val Cys Thr Lys Asn Leu
                165                 170                 175

Leu Leu Ala Arg Glu Gly Ile Asp Ser Glu Cys Gly Pro Phe Ile Lys
            180                 185                 190

Leu Ser Asp Pro Gly Ile Pro Ile Thr Val Leu Ser Arg Gln Glu Cys
            195                 200                 205

Ile Glu Arg Ile Pro Trp Ile Ala Pro Glu Cys Val Glu Asp Ser Lys
    210                 215                 220

Asn Leu Ser Val Ala Ala Asp Lys Trp Ser Phe Gly Thr Thr Leu Trp
225                 230                 235                 240

Glu Ile Cys Tyr Asn Gly Glu Ile Pro Leu Lys Asp Lys Thr Leu Ile
            245                 250                 255

Glu Lys Glu Arg Phe Tyr Glu Ser Arg Cys Arg Pro Val Thr Pro Ser
            260                 265                 270

Cys Lys Glu Leu Ala Asp Leu Met Thr Arg Cys Met Asn Tyr Asp Pro
            275                 280                 285

Asn Gln Arg Pro Phe Phe Arg Ala Ile Met Arg Asp Ile Asn Lys Leu
    290                 295                 300

Glu Glu Gln Asn Pro Asp Ile
305                 310

<210> SEQ ID NO 12
<211> LENGTH: 8
<212> TYPE: PRT
<213> ORGANISM: Artificial
<220> FEATURE:
<223> OTHER INFORMATION: Synthetic construct

<400> SEQUENCE: 12

Val Val Gly Ala Val Gly Val Gly
1               5

<210> SEQ ID NO 13
<211> LENGTH: 189
```

-continued

```
<212> TYPE: PRT
<213> ORGANISM: Homo sapiens

<400> SEQUENCE: 13

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

KRAS G12V MUTANT BINDS TO JAK1, INHIBITORS, PHARMACEUTICAL COMPOSITIONS, AND METHODS RELATED THERETO

CROSS-REFERENCE TO RELATED APPLICATIONS

This application is the National Stage of International Application No. PCT/US2020/036077 filed Jun. 8, 2020, which claims the benefit of U.S. Provisional Application No. 62/858,472 filed Jun. 7, 2019. The entirety of each of these applications is hereby incorporated by reference for all purposes.

STATEMENT REGARDING FEDERALLY SPONSORED RESEARCH OR DEVELOPMENT

This invention was made with government support under CA217875 awarded by the National Institutes of Health. The government has certain rights in this invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 19183PCT_ST25.txt. The text file is 8,886 bytes, was created on Jun. 8, 2020, and is being submitted electronically via EFS-Web. No new matter has been added.

BACKGROUND

The Kirsten rat sarcoma viral oncogene homolog (KRAS) mutations exist in various cancers, especially pancreatic, lung and colorectal cancer. KRAS mutations have been correlated with poor prognosis and poor response to chemotherapy. As a family, RAS proteins are binary switches, cycling between the inactive GDP-bound form and the activated GTP-bound form. Mutations in KRAS are often associated with enhanced GTP-bound activated conformation which provokes uncontrolled cell proliferative signaling. Therapeutic candidates that specifically target tumors with a particular mutation in KRAS are being evaluated for mutation-directed therapeutic strategies. Canon et al. report the clinical KRAS mutant G12C inhibitor AMG 510 drives anti-tumor immunity. Nature, 2019, 575, 217-223. $KRAS^{G12C}$-targeted drugs are being tested in clinical trials.

Checkpoint inhibitors such as PD-1 antibodies have become a promising avenue for cancer treatment. However, initial tumor regression in response to anti-PD-1 therapy is sometimes followed by disease progression. Zaretsky et al. report whole-exome sequencing detected clonal selection and outgrowth of the acquired resistant tumors and revealed resistance-associated loss-of-function mutations in the genes encoding interferon-receptor-associated Janus kinase 1 (JAK1) or Janus kinase 2 (JAK2). N Engl J Med, 2016, 375:819-829. They concluded that acquired resistance to PD-1 blockade immunotherapy in patients with melanoma was associated with defects in the pathways involved in interferon-receptor signaling and in antigen presentation.

References cited herein are not an admission of prior art.

SUMMARY

This disclosure relates to the discovery that a G12V mutant of KRAS (hereinafter KRAS G12V) binds to JAK1, i.e., the existence of a KRAS G12V and JAK1 binding interaction. In certain embodiments, this disclosure relates to methods of disrupting the KRAS G12V and JAK1 interaction reversing KRAS G12V induced immune escape by cancer cells utilizing agents that prevent the binding of JAK1 to KRAS G12V. In certain embodiments, the agent is a cell permeable peptide having the sequence $X^1$DYKDDEG (SEQ ID NO: 3) or derivative thereof, wherein $X^1$ is any amino acid, such as the peptides MDYKDDEG (SEQ ID NO: 1) and ADYKDDEG (SEQ ID NO: 2).

In certain embodiments, this disclosure relates to methods of treating cancer comprising administering an effective amount of an agent that is a binding inhibitor of KRAS G12V to JAK1 to a subject in need thereof. In certain embodiments, the agent is a peptide or small molecule. In certain embodiments, the agent is a peptide conjugated to a ligand of a E3 ubiquitin ligase. In certain embodiments, the agent is an antibody with an epitope to JAK1 sequence MDYKDDEG (SEQ ID NO: 1) which interacts with the KRAS G12V mutant sequence. In certain embodiments, the agent is an antibody with an epitope to the KRAS G12V mutant sequence, e.g., VVGAVGVG (SEQ ID NO: 12). In certain embodiments, the agent is a peptide having the amino acid sequence $X^1$DYKDDEG (SEQ ID NO: 3), derivative, or conjugate thereof, wherein $X^1$ is any amino acid. In certain embodiments, the peptide has the amino acid sequence MDYKDDEG (SEQ ID NO: 1) or ADYKDDEG (SEQ ID NO: 2) or derivative thereof.

In certain embodiments, this disclosure relates to methods of treating patients with KRAS G12V cancer or carrying tumors with agents disclosed herein. In certain embodiments, patients are diagnosed with a KRAS G12V mutation. In certain embodiments, patients are diagnosed with pancreatic cancer, lung cancer, colorectal cancer, uterine cancer, and gastric cancer.

In certain embodiments, the agent is administered in combination with another chemotherapy agent. In certain embodiments, the other chemotherapy agent is an immune checkpoint inhibitor. In certain embodiments, checkpoint inhibitor is an anti-CTLA-4 antibody, anti-PD-1 antibody, anti-PD-L1 antibody, or combinations thereof. In certain embodiments, the checkpoint inhibitor is ipilimumab, nivolumab, pembrolizumab, cemiplimab, atezolizumab, durvalumab, avelumab, or combinations thereof.

In certain embodiments, this disclosure relates to anticancer agents that are KRAS G12V mutation directed, immune re-activators. In certain embodiments, the binding inhibitors of KRAS G12V to JAK1 are small molecules. In certain embodiments, this disclosure relates to methods of discovering small molecule binding inhibitors of the KRAS G12V-JAK1 interaction. In certain embodiments, this disclosure relates to methods of screening for agents that are binding inhibitors of the KRAS G12V-JAK1 interaction comprising mixing a test agent with JAK1 and KRAS having a G12V mutation and determining whether the test agent reduces the ability of JAK1 to bind with KRAS G12V. In certain embodiments, the test agent is a peptide, nucleic acid, antibody, steroid, or small molecule.

In certain embodiments, this disclosure relates to uses of agents disclosed herein as a targeting agent. In certain embodiments, this disclosure relates targeted therapies using conjugate proteins that degrade KRAS G12V cancers or tumors. In certain embodiments, this disclosure relates to using RasKi to target KRAS G12V for degradation. In certain embodiments, targeting peptides have the amino acid sequence $X^1$DYKDDEG (SEQ ID NO: 3), MDYKDDEG (SEQ ID NO: 1), ADYKDDEG (SEQ ID NO: 2), or derivatives thereof and are conjugated or fused to a molecule or peptide that the binds to an E3 ubiquitin ligase. In certain embodiment, the conjugates or fusions are pharmaceutical compositions for use in cancer treatment. In certain embodiment, this disclosure relates to methods of treating cancer comprising administering an effective amount a conjugate or fusion peptide comprising $X^1$DYKDDEG (SEQ ID NO: 3), MDYKDDEG (SEQ ID NO: 1), ADYKDDEG (SEQ ID NO: 2), or derivatives thereof are conjugated or fused to E3 ubiquitin ligase binder to a subject in need thereof.

In certain embodiments, this disclosure relates to peptides having the amino acid sequence $X^1$DYKDDEG (SEQ ID NO: 3) or derivatives thereof conjugated or linked to a toxin or a protease, wherein $X^1$ is any amino acid. In certain embodiments, the toxin is a radioactive isotope. In certain embodiments, the peptide has the amino acid sequence MDYKDDEG (SEQ ID NO: 1) or ADYKDDEG (SEQ ID NO: 2).

In certain embodiments, this disclosure relates to uses of agents disclosed herein as biosensors for monitoring KRAS G12V mutations in cancer or tumors. In certain embodiments, this disclosure relates to peptides having the amino acid sequence $X^1$DYKDDEG (SEQ ID NO: 3) or derivatives thereof, wherein $X^1$ is any amino acid, wherein the peptide has a label. In certain embodiments, the label is a fluorescent dye, fluorescent nanoparticle, fluorescent peptide, a fluorescent quencher, ligand to a receptor, biotin, antibody, or radioactive isotope contained within or conjugated to the peptide. In certain embodiments, the peptide has the amino acid sequence MDYKDDEG (SEQ ID NO: 1) or ADYKDDEG (SEQ ID NO: 2).

In certain embodiments, this disclosure relates to methods of using an agent or a labeled agent for detecting KRAS G12V mutations comprising mixing a sample suspected of containing cancerous cells, e.g., a blood sample or a tumor biopsy, and an agent disclosed herein, such as peptides having or consisting of the amino acid sequence $X^1$DYKDDEG (SEQ ID NO: 3) or derivatives thereof, wherein $X^1$ is any amino acid, or an agent disclosed herein conjugated to a label and scanning or searching the sample for the distribution of the agent in the sample, e.g., concentration of the labeled agent in a specific area of the sample, and imaging the sample, e.g., visually, photographically, by video camera, or other detection means, and optionally storing the image on a computer readable medium.

In certain embodiments, this disclosure relates to methods of using imaging agents for detecting KRAS G12V mutations comprising administering an agent disclosed herein, such as peptides having or consisting of the amino acid sequence $X^1$DYKDDEG (SEQ ID NO: 3) or derivatives thereof, wherein $X^1$ is any amino acid, or an agent disclosed herein conjugated to a label and scanning or searching the subject for the distribution of the agent in a tissue, area, or specific location of the subject.

In certain embodiments, this disclosure relates to methods comprising administering a composition comprising an agent disclosed herein, such as peptides having or consisting of the amino acid sequence $X^1$DYKDDEG (SEQ ID NO: 3) or derivatives thereof, optionally containing a label such as a radionuclide to a subject; and scanning the subject to determine the location or an emission of the agent. In certain embodiments, the method further comprises the step of detecting the location and creating an image indicating or highlighting the location of the agent in the subject, e.g. by x-ray, magnetic resonance imaging (MRI), computed (axial) tomography scan, PET imaging or combinations thereof.

In certain embodiments, this disclosure relates to peptides having or consisting of the amino acid sequence $X^1$DYKDDEG (SEQ ID NO: 3) or derivatives thereof, wherein $X^1$ is any amino acid. In certain embodiments, the N-terminus of a peptide may consist of an amino acid sequence $X^1$DYKDDEG (SEQ ID NO: 3) or derivatives thereof, wherein $X^1$ is any amino acid. In certain embodiments, the C-terminus of a peptide may consist of an amino acid sequence $X^1$DYKDDEG (SEQ ID NO: 3) or derivatives thereof, wherein $X^1$ is any amino acid.

In certain embodiments, the peptide has or consists of the amino acid sequence MDYKDDEG (SEQ ID NO: 1) or ADYKDDEG (SEQ ID NO: 2). In certain embodiments, the N-terminus of a peptide may consist of an amino acid sequence MDYKDDEG (SEQ ID NO: 1) or ADYKDDEG (SEQ ID NO: 2). In certain embodiments, the C-terminus of a peptide may consist of an amino acid sequence MDYKD-DEG (SEQ ID NO: 1) or ADYKDDEG (SEQ ID NO: 2).

In certain embodiments, the disclosure contemplates peptides disclosed herein having at least one molecular modification, e.g., such that the peptide contains a non-naturally amino acid. In certain embodiments, the disclosure contemplates a non-naturally occurring derivative of a peptide having SEQ ID NO: 1-3, variants, or derivatives thereof. In certain embodiments, the disclosure contemplates a derivative in the form of a prodrug. In certain embodiments, the disclosure contemplates a derivative wherein an amino, carboxyl, hydroxyl, or thiol group in a peptide disclosed herein is substituted. In certain embodiments, the disclosure contemplates peptides disclosed herein having a label, e.g., fluorescent or radioactive.

In certain embodiments, the peptide is N-terminal substituted with a heterologous peptide. In certain embodiments, the peptide is C-terminal substituted with a heterologous peptide. In certain embodiments, the peptide is N-terminal substituted with an alkanoyl, wherein alkanoyl is optionally substituted. In certain embodiments, alkanoyl is optionally substituted with a hydrophilic polymer such as polyethylene glycol. In certain embodiments, the peptide has C-terminal amide, wherein the amide is optionally substituted with alkyl. In certain embodiments, one or more carboxylic acid groups in the peptide are converted to alkyl esters such ethyl esters. In certain embodiments, the peptide has a molecular weight of less than 2, 3, 4, or 5 kilodalton (kDa). In certain embodiments, the peptide has a molecular weight of less than 10, 20, or 30 kilodalton (kDa).

In certain embodiments, the peptides discloses herein have at least one non-naturally occurring molecular modification, such as the attachment of polyethylene glycol, the attachment of a heterologous peptide, the attachment of a fluorescent dye comprising aromatic groups, fluorescent peptide, a chelating agent capable of binding a radionuclide such as 18F, N-terminal acetyl, propionyl group, myristoyl and palmitoyl, group or N-terminal methylation, or a C-terminal alkyl ester. In certain embodiments, the disclosure contemplates peptides disclosed herein labeled using biotinylation reagents. Biotinylated peptides can be used in streptavidin affinity binding, purification, and detection. In certain embodiments, the disclosure contemplates peptides disclose herein containing azide-derivatives of naturally occurring monosaccharides such as N-azidoacetylglucosamine, N-azidoacetylmannosamine, and N-azidoacetylgalactosamine.

In certain embodiments, this disclosure contemplates derivatives of peptide disclose herein wherein one or more amino acids are substituted with chemical groups to improve pharmacokinetic properties such as solubility and serum half-life, optionally connected through a linker. In certain embodiments, such a derivative may be a prodrug wherein the substituent or linker is biodegradable, or the substituent or linker is not biodegradable. In certain embodiments, contemplated substituents include a saccharide, polysaccharide, acetyl, fatty acid, lipid, and/or polyethylene glycol. The substituent may be covalently bonded through the formation of amide bonds on the C-terminus or N-terminus of the peptide optionally connected through a linker. In certain embodiments, it is contemplated that the substituent may be covalently bonded through an amino acid within the peptide, e.g. through an amine side chain group such as lysine or an amino acid containing a carboxylic acid side chain group such as aspartic acid or glutamic acid, within the peptide comprising a sequence disclosed herein. In certain embodiments, it is contemplated that the substituent may be covalently bonded through a cysteine in a sequence disclosed herein optionally connected through a linker. In certain embodiments, a substituent is connected through a linker that forms a disulfide with a cysteine amino acid side group.

In certain embodiments, the disclosure relates to recombinant vectors comprising a nucleic acid encoding peptide disclosed herein. In certain embodiments, the disclosure relates to expression systems comprising a recombinant vector comprising a nucleic acid encoding peptide disclosed herein. In certain embodiments, the disclosure relates to cells comprising a recombinant vector comprising a nucleic acid encoding peptide disclosed herein. In certain embodiments, the disclosure relates to a vector comprising the nucleic acid encoding a peptide disclosed herein and a heterologous nucleic acid sequence.

In certain embodiments, the disclosure relates to a nucleic acid encoding a polypeptide disclosed herein wherein the nucleotide sequence has been changed to contain at least one non-naturally occurring substitution and/or modification relative to the naturally occurring sequence, e.g., one or more nucleotides have been changed relative to the natural sequence.

In certain embodiments, this disclosure relates to antibodies that specifically bind a peptide having the amino acid sequence $X^1$DYKDDEG (SEQ ID NO: 3) wherein $X^1$ is an amino acid, MDYKDDEG (SEQ ID NO: 1), or ADYKDDEG (SEQ ID NO: 2).

In certain embodiments, this disclosure relates to pharmaceutical composition comprising binding inhibitors of the KRAS G12V-JAK1 interaction such as a peptide having the amino acid sequence $X^1$DYKDDEG (SEQ ID NO: 3) or derivatives thereof, wherein $X^1$ is any amino acid, MDYKDDEG (SEQ ID NO: 1), or ADYKDDEG (SEQ ID NO: 2) and a pharmaceutically acceptable excipient.

BRIEF DESCRIPTION OF THE SEVERAL VIEWS OF THE DRAWINGS

FIG. 1 illustrates two peptide inhibitors of KRAS G12V binding to JAK1, top, 8-mer (RasKi, SEQ ID NO: 1), and bottom 8-mer (M603A mutant, SEQ ID NO: 2).

FIG. 2A shows a sequence alignment (SEQ ID NO: 4, SEQ ID NO: 5, SEQ ID NO: 6 and SEQ ID NO: 7) of the T4a region in JAK1 in comparisons with the same region of other three JAK family members. Right panel shows results of the GST-affinity pull-down assay, showing 8-mer (RasKi, SEQ ID NO: 1) is involved in binding with KRAS-G12V.

FIG. 2B shows data indicating disruption of the KRAS-G12V interaction with JAK1 by RasKi (8-mer). TR-FRET titration assay was performed with HEK293T lysate that had been co-transfected with His-KRAS-G12V and Flag-JAK1. TR-FRET signals were recorded upon treatment with the synthetic peptide 8-mer (RasKi) or the 9-mer control (0 to 50 μM).

FIG. 2C shows data of GST-affinity pull-down assay indicating that 8-mer (RasKi) can compete with JAK1 full length for binding to KRAS-G12V.

FIG. 2D shows data indicating RasKi (8-mer) specifically inhibits the KRAS-G12V-JAK1 interaction in a TR-FRET assay. Cell lysate from HEK293T cells co-expressing GST-KRAS-G12V and Venus-Flag-JAK1 was treated with the synthetic peptide 8-mer WT (MDYKDDEG, SEQ ID NO: 1) or an 8-mer with K606E mutation. A panel of mutations in 8-mer (5 μM) were tested including M603A (ADYKDDEG, SEQ ID NO: 2).

FIG. 2E shows data from a GST-KRAS pull down assay indicating the inhibitory effect of 8-mer (WT) on the KRAS-G12V-JAK1 interaction compared with the 8-mer/K606E control.

FIG. 2F shows data from a GST-affinity pull-down assay performed to detect the competition effect of the 8-mer (WT), or 8-mer K606E peptide on the KRAS-G12V/JAK1 interaction under endogenous conditions.

FIG. 2G shows data on a GST-affinity pull-down assay indicating the interaction of KRAS-G12V with pseudokinase domain or its mutant form, PK-K606E.

FIG. 3A shows data on the effect of KRAS-G12V overexpression and RasKi on IFN-γ stimulated STAT1 transcription. STAT1 transcriptional activity was tested in HEK293T cells with a dual-luciferase assay. Luciferase activity was measured upon co-expression of JAK1 and KRAS WT, G12V, or G12V with 8-mer. Fold of Control (FOC) with IFN-γ stimulation was calculated comparing to samples without IFN-γ stimulation. Cells were treated with 1 ng/ml IFN-γ for 18 hours after 24 hours of transfection. Dual-luciferase assays were performed, and relative luciferase activity was measured normalized to *Renilla* luciferase control.

FIG. 3B shows data on the effect of KRAS-G12V overexpression and RasKi on IFN-γ stimulated pathway activation. Western Blot was performed to detect the JAK-STAT pathway signaling change in HEK293T cells with overexpressed JAK1 along with KRAS-WT, G12V, or G12V with 8-mer, with or without IFN-γ stimulation (1 ng/ml, 30 minutes). FOC bar graphs show the levels of phosphorylated STAT1 and STAT3 phosphorylation, and the expression of IRF1 and TAP1 after IFN-γ stimulation in comparison to that without stimulation.

FIG. 4A shows data on IFNγ-induced cell death in KRAS-WT and G12V isogenic cells with or without transduced RasKi (8-mer). Bar graphs show the cell death of three pairs of KRAS isogenic cell lines SW48, LIM1215, H838 under different treatment conditions. No cell killing effect was seen in cells treated with 8-mer without IFNγ.

FIG. 4B shows data on inhibition of JAK, or IFNγ receptor activity, blocked cell killing induced by the combination of RasKi and IFNγ. Bar graphs show cell death in three KRAS isogenic G12V cell lines in response to IFNγ stimulation and 8-mer peptide, with or without treatment with a JAK1 inhibitor or an IFNγ-receptor antagonist.

FIG. 4C shows data on NK92 cell-induced death of KRAS-WT and G12V isogenic cells with or without transduced RasKi (8-mer). Dose-dependent killing curves of RasKi/8-mer peptide are shown for KRAS WT and G12V isogenic SW48, LIM1215, H838 cell lines with or without NK92 cell stimulation from cell viability readouts.

FIG. 4D shows NK92-induced death of KRAS isogenic cells with RasKi (8-mer) requires active JAK and IFNγ-receptor. RasKi dose-dependent cell death curves were established for KRAS isogenic cell lines treated with JAK1 inhibitor or IFNγ-receptor antagonist in response to NK92 cell stimulation. Bar graphs show integrated results from area under curve (AUC) data of each treatment condition.

FIG. 5A shows data on the effect of RasKi on response of KRASG12V cells to T cell-mediated immune killing in the isogenic cancer cells reversing immune escape of KRASG12V from cytotoxic T cells. The lentivirus-transduced HLA-A2+ parental KRAS WT cells, SW48-A2+ and their KRAS G12V knock-in isogenic cells were co-cultured with anti-NY-ESO-1 CD8+ T cells, or treated with RasKi, RasKi-K606E, or in combinations as indicated. The cell viability after treatment was measured using CellTiter Blue™ reagent. The growth inhibition was normalized to the untreated control.

FIG. 5B shows data for LIM1215-A2+ cells.

FIG. 5C shows data for H838-A2+ cells.

FIG. 5D shows data on T cell-mediated immune killing in the patient-derived colon cancer cells. The lentivirus-transduced HLA-A2+ patient derived KRAS WT colon cancer cells (SW48-A2+, LIM1215-A2+ and Caco-2-A2+) and KRASG12V colon cancer cells (SW403-A2+, SW480-A2+ and SW620-A2+) were co-cultured with anti-NY-ESO-1 CD8+ T cells, or treated with RasKi, RasKi-K606E, or in combinations as indicated. The cell viability after treatment was measured using CellTiter Blue™ reagent. The growth inhibition was normalized to the untreated control.

FIG. 5E shows data indicating an effect of IFNγ/JAK/STAT pathway inhibition of HLA-A2+ KRASG12V cells on the response to T cell-mediated immune killing. The G12V isogenic cells (SW48G12V-A2+, LIM1215G12V-A2+ and H838G12V-A2+) and were co-cultured with anti-NY-ESO-1

Figure 3C:
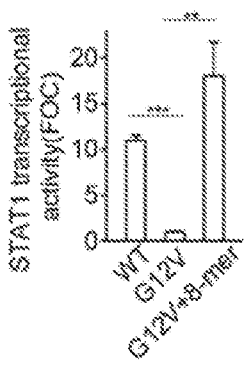
FIG. 3C shows data on the effect of KRAS-G12V and RasKi on IFN-γ stimulated STAT1 transcription activity under endogenous conditions. FOC (Fold of control) of STAT1 transcriptional activity was calculated in SW48 (KRAS isogenic colon cancer) WT and G12V cell lines with IFN-γ stimulation comparing to that without IFN-γ stimulation. RasKi was transduced into G12V cells by lentivirus. Cells were treated with IFN-γ (1 ng/ml) for 18 hours after 24 hours of transduction. Dual-luciferase assays were performed, and relative luciferase activity was measured, normalized to *Renilla* luciferase control.

CD8+ T cells and treated with RasKi, or in addition with JAK inhibitor (JAKi) or IFNγ receptor antagonist (IFNγRa) as indicated. The cell viability after treatment was measured using CellTiter Blue™ reagent. The growth inhibition was normalized to the untreated control. Each dot represents an individual cell line.

FIG. 5F shows data on a patient derived colon cancer cells harboring KRASG12V mutations (SW403-A2+, SW480-A2+ and SW620-A2+).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps.

"Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a range of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a range of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a range of amino acids specified in the claim however the N-terminus may be connected to additional amino acids, e.g., as part of a larger peptide.

"Subject" refers to any animal, preferably a human patient, livestock, rodent, monkey or domestic pet.

"Cancer" refers any of various cellular diseases with malignant neoplasms characterized by the proliferation of cells. Cancer may or may not be present as a tumor mass with a defined boundary. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

The term "effective amount" refers to that amount of a compound or pharmaceutical composition described herein that is sufficient to effect the intended application including, but not limited to, disease treatment, as illustrated below. In relation to a combination therapy, an "effective amount" indicates the combination of agent results in synergistic or additive effect when compared to the agents individually. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, the term "small molecule" refers to any variety of covalently bound molecules with a molecular weight of less than 900 or 1000. Typically, the majority of atoms include carbon, hydrogen, oxygen, nitrogen, and to a lesser extent sulfur and/or a halogen. Examples include steroids, short peptides, mono or polycyclic aromatic or non-aromatic, heterocyclic compounds.

A "chemotherapy agent," "chemotherapeutic," "anti-cancer agent," or the like, refer to molecules that are recognized to aid in the treatment of a cancer. Contemplated examples include the following molecules or derivatives such as abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, ruca-parib, siltuximab, sunitinib, thioguanine, temsirolimus, tha-lidomide, thiotepa, trabectedin, valrubicin, vandetanib, vin-blastine, vemurafenib, vorinostat, zoledronic acid, or combinations thereof such as cyclophosphamide, methotr-exate, 5-fluorouracil (CMF); doxorubicin, cyclophosph-amide (AC); mustine, vincristine, procarbazine, predniso-lone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

The terms "protein," "peptide," and "polypeptide" refer to compounds comprising amino acids joined via peptide bonds and are used interchangeably. As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit be limited to natural amino acids. The term includes non-naturally occurring amino acids and modifications such as, substitutions, gly-cosylations, and addition of hydrophilic or lipophilic moi-eties.

In the context of a fusion or chimeric peptide (a peptide comprising two or more peptide segments), a "heterolo-gous" peptide sequence is a comparative term and refers to a peptide segment that would not naturally occur together with the other segment, e.g., because one the of the segments is derived from a different organism, a label, or random. In certain embodiments, a heterologous fusion peptide of this disclosure may contain a peptide sequence disclosed herein and a fluorescent protein sequence, a protease cleaving sequence, a self-cleaving sequence, a ligand, antibody epitope, or a polyhistidine sequence.

As used herein, the term "conjugated" refers to linking molecular entities through covalent bonds, or by other specific binding interactions, such as due to hydrogen bond-ing and other van der Walls forces. The force to break a covalent bond is high, e.g., about 1500 pN for a carbon to carbon bond. The force to break a combination of strong protein interactions is typically a magnitude less, e.g., biotin to streptavidin is about 150 pN. Thus, a skilled artisan would understand that conjugation must be strong enough to bind molecular entities in order to implement the intended results.

A "linking group" refers to any variety of molecular arrangements that can be used to bridge to molecular moi-eties together. An example formula may be $—R_n—$ wherein R is selected individually and independently at each occur-rence as: $—CR_nR_n—$, $—CHR_n—$, $—CH—$, $—C—$, $—CH_2—$, $—C(OH)R_n—$, $—C(OH)(OH)—$, $—C(OH)$ H, $—C(Hal)R_n—$, $—C(Hal)(Hal)-$, $—C(Hal)H—$, $—C(N_3)$ $R_n—$, $—C(CN)R_n—$, $—C(CN)(CN)—$, $—C(CN)$ H—, $—C(N_3)(N_3)—$, $—C(N_3)H—$, $—O—$, $—S—$, $—N—$, $—NH—$, $—NR_n—$, $(C\!=\!O)—$, $—(C\!=\!NH)—$, $—(C\!=\!S)—$, $—(C\!=\!CH_2)—$, which may contain single, double, or triple bonds individually and independently between the R groups. If an R is branched with an $R_n$ it may be terminated with a group such as $—CH_3$, $—H$, $—CH\!=\!CH_2$, $—CCH$, $—OH$, $—SH$, $—NH_2$, $—N_3$, $—CN$, or -Hal, or two branched Rs may form an aromatic or non-aromatic cyclic structure. It is contemplated that in certain instances, the total Rs or "n" may be less than 100 or 50 or 25 or 10. Examples of linking groups include bridging alkyl groups and alkoxyalkyl groups.

As used herein, the term "ligand" refers to any organic molecule, i.e., substantially comprised of carbon, hydrogen, and oxygen, that specifically binds to a "receptor." Recep-tors are organic molecules typically found on the surface of a cell. Through binding a ligand to a receptor, the cell has a signal of the extra cellular environment which may cause changes inside the cell. As a convention, a ligand is usually used to refer to the smaller of the binding partners from a size standpoint, and a receptor is usually used to refer to a molecule that spatially surrounds the ligand or portion thereof. However as used herein, the terms can be used interchangeably as they generally refer to molecules that are specific binding partners. For example, a glycan may be expressed on a cell surface glycoprotein and a lectin protein may bind the glycan. As the glycan is typically smaller and surrounded by the lectin protein during binding, it may be considered a ligand even though it is a receptor of the lectin binding signal on the cell surface. An antibody may be a receptor, and the epitope may be considered the ligand. In certain embodiments, a ligand is contemplated to be a compound that has a molecular weight of less than 500 or 1,000. In certain embodiments, a receptor is contemplated to be a proteinaceous compound that has a molecular weight of greater than 1,000, 2,000 or 5,000.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive iso-topes. In one example, a peptide "label" refers to incorpo-ration of a heterologous polypeptide in the peptide, wherein the heterologous sequence can be identified by a specific binding agent, antibody, or bind to a metal such as nickel/nitrilotriacetic acid, e.g., a polyhistidine sequence. Specific binding agents and metals can be conjugated to solid sur-faces to facilitate purification methods. A label includes the incorporation of a radiolabeled amino acid or the covalent attachment of biotinyl moieties to a polypeptide that can be detected by marked avidin (for example, streptavidin con-taining a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, lucifer-ase, alkaline phosphatase), chemiluminescent markers, biotinyl groups, predetermined polypeptide epitopes recog-nized by a secondary reporter (such as a leucine zipper pair sequences, binding sites for secondary antibodies, metal binding domains, epitope tags), or magnetic agents, such as gadolinium chelates. In some embodiments, labels may be attached by spacer arms of various lengths to reduce poten-tial steric hindrance.

The term "radionuclide" or "radioactive isotope" refers to molecules of enriched isotopes that exhibit radioactive decay (e.g., emitting positrons). Such isotopes are also referred to in the art as radioisotopes. A radionuclide tracer does not include radioactive primordial nuclides, but does include a naturally occurring isotopes that exhibit radioac-tive decay with an isotope distribution that is enriched, e.g., is several fold greater than natural abundance. In certain embodiments, is contemplated that the radionuclides are limited to those with a half live of less than 1 hour and those with a half-life of more than 1 hour but less than 24 hours.

Radioactive isotopes are named herein using various commonly used combinations of the name or symbol of the element and its mass number (e.g., $^{18}$F, F-18, or fluorine-18).

The term "specific binding agent" refers to a molecule, such as a proteinaceous molecule, that binds a target molecule with a greater affinity than other random molecules or proteins. Examples of specific binding agents include antibodies that bind an epitope of an antigen or a receptor which binds a ligand. "Specifically binds" refers to the ability of a specific binding agent (such as an ligand, receptor, enzyme, antibody or binding region/fragment thereof) to recognize and bind a target molecule or polypeptide, such that its affinity (as determined by, e.g., affinity ELISA or other assays) is at least 10 times as great, but optionally 50 times as great, 100, 250 or 500 times as great, or even at least 1000 times as great as the affinity of the same for any other or other random molecule or polypeptide.

In certain contexts, an "antibody" refers to a protein based molecule that is naturally produced by animals in response to the presence of a protein or other molecule or that is not recognized by the animal's immune system to be a "self" molecule, i.e. recognized by the animal to be a foreign molecule and an antigen to the antibody. The immune system of the animal will create an antibody to specifically bind the antigen, and thereby targeting the antigen for elimination or degradation. It is well recognized by skilled artisans that the molecular structure of a natural antibody can be synthesized and altered by laboratory techniques. Recombinant engineering can be used to generate fully synthetic antibodies or fragments thereof providing control over variations of the amino acid sequences of the antibody. Thus, as used herein the term "antibody" is intended to include natural antibodies, monoclonal antibody, or non-naturally produced synthetic antibodies, and binding fragments, such as single chain binding fragments. These antibodies may have chemical modifications. The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same antigen. The term "monoclonal" is not limited to any particular method for making the antibody, nor is the term limited to antibodies produced in a particular species, e.g., mouse, rat, etc.

From a structural standpoint, an antibody is a combination of proteins: two heavy chain proteins and two light chain proteins. The heavy chains are longer than the light chains. The two heavy chains typically have the same amino acid sequence. Similarly, the two light chains have the same amino acid sequence. Each of the heavy and light chains contain a variable segment that contains amino acid sequences which participate in binding to the antigen. The variable segments of the heavy chain do not have the same amino acid sequences as the light chains. The variable segments are often referred to as the antigen binding domains. The antigen and the variable regions of the antibody may physically interact with each other at specific smaller segments of an antigen often referred to as the "epitope." Epitopes usually consist of surface groupings of molecules, for example, amino acids or carbohydrates. The terms "variable region," "antigen binding domain," and "antigen binding region" refer to that portion of the antibody molecule which contains the amino acid residues that interact with an antigen and confer on the antibody its specificity and affinity for the antigen. Small binding regions within the antigen-binding domain that typically interact with the epitope are also commonly alternatively referred to as the "complementarity-determining regions, or CDRs."

Hydrophilic polymers contain polar or charged functional groups, rendering them soluble in water. Examples include polyethylene glycol, polylactides, polyglycolide, poly(ε-caprolactone), poly(2-methoxyethyl acrylate), poly(tetrahydrofurfuryl acrylate), poly(2-methacryloyloxyethyl phosphorylcholine), poly(p-dioxanone), poly(serine methacrylate), poly[oligo(ethylene glycol) vinyl ether], poly{[2-(methacryloyloxy)ethyl], copolymers of ethylene glycol and propylene glycol, poly(oxyethylated polyol), poly(olefmic alcohol), poly(vinylpyrrolidone), poly(hydroxyalkylmethacrylamide), poly(hydroxyalkylmethacrylate), poly(saccharides), poly(alpha-hydroxy acid), and poly (vinyl alcohol). "PEG," "polyethylene glycol" and "poly (ethylene glycol)" refers to water-soluble poly(ethylene oxide). Typically, PEGs comprise the following structure "—$(OCH_2CH_2)n$-" where (n) is 2 to 4000.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom, replacing an amino group with a hydroxyl group, replacing a nitrogen with a protonated carbon (CH) in an aromatic ring, replacing a bridging amino group (—NH—) with an oxy group (—O—), or vice versa. The derivative may be a prodrug. A derivative may be a polypeptide variant. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(—O)NRaNRb, —NRaC(=O) ORb, —NRaSO2Rb, —C(=O)Ra, —C(=O) ORa, —C(=O) NRaRb, —OC(=O) NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkanoyl" refers to an alkyl as defined above with the indicated number of carbon atoms attached through a carbonyl bride (i.e., —(C=O)alkyl).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters of carboxylic acids, e.g., ethyl esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "recombinant" when made in reference to a nucleic acid molecule refers to a nucleic acid molecule which is comprised of segments of nucleic acid joined together by means of molecular biological techniques provided that the entire nucleic acid sequence does not occurring in nature, i.e., there is at least one mutation in the overall sequence such that the entire sequence is not naturally occurring even though separately segments may occurring in nature. The segments may be joined in an altered arrangement such that the entire nucleic acid sequence from start to finish does not naturally occur. The term "recombinant" when made in reference to a protein or a polypeptide refers to a protein molecule that is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Proteins may be recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38 (13): e141, both hereby incorporated by reference in their entirety.

Methods of Use

In certain embodiments, this disclosure relates to methods of inhibiting KRAS G12V-mediated cell signaling to JAK1 comprising contacting a cell with an effective amount of one or more agents disclosed herein. In certain embodiments, this disclosure relates to using the agents or pharmaceutical compositions of the present disclosure to treat diseases or conditions, including but not limited to conditions implicated by KRAS G12V mutations (e.g., cancer). In some embodiments, this disclosure relates to methods of treating of cancer comprising administering an effective amount of a pharmaceutical composition comprising an agent as disclosed herein to a subject in need thereof. In some embodiments, the cancer is mediated by a KRAS G12V mutation. In various embodiments, the cancer is pancreatic cancer, colorectal cancer or lung cancer. In some embodiments, the cancer is gall bladder cancer, thyroid cancer, and bile duct cancer.

In certain embodiments, this disclosure relates to methods of treating a disorder in a subject in need thereof, wherein the said method comprises determining if the subject has a KRAS G12V mutation and if the subject is determined to have the KRAS G12V mutation, then administering to the subject a therapeutically effective dose of at least one agent as disclosed herein or a pharmaceutically acceptable salt thereof.

In certain embodiments, disclosed agents prevent anchorage-independent cell growth and therefore have the potential to prevent tumor metastasis. In certain embodiments, this disclosure relates to methods of preventing tumor metastasis, the method comprising administering an effective amount an agent disclosed herein.

KRAS mutations have been identified in hematological malignancies (e.g., cancers that affect blood, bone marrow and/or lymph nodes). Accordingly, in certain embodiments methods are directed to administration of a disclosed agent (e.g., in the form of a pharmaceutical composition) to a patient in need of treatment of a hematological malignancy. Such malignancies include leukemias and lymphomas. For example, the presently disclosed agents can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMA) and/or other leukemias. In other embodiments, the agents are useful for treatment of lymphomas such as all subtypes of Hodgkin's lymphoma or non-Hodgkin's lymphoma. In various embodiments, the compounds are useful for treatment of plasma cell malignancies such as multiple myeloma.

Determining whether a tumor or cancer comprises a KRAS G12V mutation can be undertaken by assessing a nucleotide sequence encoding the KRAS protein, by assessing the amino acid sequence of the KRAS protein, or by assessing the characteristics of a putative KRAS mutant protein. GTPase KRas isoform a [*Homo sapiens*] is provided as NCBI Reference Sequence: NP_203524.1

(SEQ ID NO: 13)

MTEYKLVVVGAGGVGKSALTIQLIQNHFVDEYDPTIEDSYRKQVVIDGETC

LLDILDTAGQEEYSAMRDQYMRTGEGFLCVFAINNTKSFEDIHHYREQIKR

VKDSEDVPMVLVGNKCDLPSRTVDTKQAQDLARSYGIPFIETSAKTRQRVE

DAFYTLVREIRQYRLKKISKEEKTPGCVKIKKCIIM.

Methods for detecting a mutation in a KRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for KRAS G12V mutations by real-time PCR. In real-time PCR, fluorescent probes specific for the KRAS G12V mutation are used. When a mutation is present, the probe binds and fluorescence is detected. In some embodiments, the KRAS G12V mutation is identified using a direct sequencing method of specific regions in the KRAS gene.

Methods for detecting a mutation in a KRAS G12V protein include detection of a KRAS mutant using a binding agent (e.g., an antibody) specific for the G12V mutant protein, protein electrophoresis, Western blotting, or direct peptide sequencing.

Methods for determining whether a tumor or cancer comprises a KRAS G12V mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

In certain embodiments, disclosure also relates to a method of treating a hyperproliferative disorder in a mammal that comprises administering to said mammal a therapeutically effective amount of an agent as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma cardiac tumors, chronic lymphocytic leukemia (CLL), chronic myelogenous leukemia (CML), colon cancer, colorectal cancer, craniopharyngioma, cutaneous T-cell lymphoma, extrahepatic ductal carcinoma in situ (DOS), embryonal tumors, CNS cancer, endometrial cancer, ependymoma, esophageal cancer, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some embodiments, the methods for treatment are directed to treating lung cancers, the methods comprise administering an effective amount of an agent disclosed herein (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

In certain embodiments, disclosure further provides methods of modulating KRAS G12V or JAK1 protein activity by contacting the protein with an effective amount of an agent of the disclosure. Modulation can be inhibiting or activating protein activity. In some embodiments, the disclosure provides methods of inhibiting protein activity by contacting the KRAS G12V or JAK1 protein with an effective amount of an agent of the disclosure in solution. In some embodiments, the disclosure provides methods of inhibiting the KRAS G12V or JAK1 protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of an agent of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS G12V or JAK1 protein activity in a cell by contacting said cell with an amount of an agent of the disclosure sufficient to inhibit the activity of KRAS G12V or JAK1 protein in said cell. In some embodiments, the disclosure provides methods of inhibiting KRAS G12V or JAK1 protein activity in a tissue by contacting said tissue with an amount of an agent of the disclosure sufficient to inhibit the activity of KRAS G12V or JAK1 protein in said tissue. In some embodiments, the disclosure provides methods of inhibiting KRAS G12V or JAK1 protein activity in an organism by contacting said organism with an amount of an agent of the disclosure sufficient to inhibit the activity of KRAS G12V or JAK1 protein in said organism. In some embodiments, the disclosure provides methods of inhibiting KRAS G12V or JAK1 protein activity in an animal by contacting said animal with an amount of an agent of the disclosure sufficient to inhibit the activity of KRAS G12V or JAK1 protein in said animal. In some embodiments, the disclosure provides methods of inhibiting KRAS G12V or JAK1 protein activity in a mammal by contacting said mammal with an amount of an agent of the disclosure sufficient to inhibit the activity of KRAS G12V or JAK1 protein in said mammal. In some embodiments, the disclosure provides methods of inhibiting KRAS G12V or JAK1 protein activity in a human by contacting said human with an amount of an agent of the disclosure sufficient to inhibit the activity of KRAS G12V or JAK1 protein in said human. The present disclosure provides methods of treating a disease mediated by KRAS G12V or JAK1 protein activity in a subject in need of such treatment.

Proteolysis-targeting chimeras (PROTACs) are conjugates or fusions that use natural proteasomes for degradation, e.g., targeting E3 ubiquitin ligase to a substrate target protein resulting in protein degradation. Proteolysis-targeting chimeras can be a peptide or a small molecule that binds to a target protein conjugated or fused to an E3 ubiquitin ligase-recruiting moiety, e.g., using a linker between the targeting protein and the E3 ligase binding moiety. The chimeras bind the target protein and E3 ubiquitin ligase to form a complex which in theory results in the ubiquitination and subsequent degradation of the target protein. See Smith et al., Differential PROTAC substrate specificity dictated by orientation of recruited E3 ligase, Nature Comm, 2019, 10, 131.

In certain embodiments, this disclosure relates to using agents disclosed herein to target KRAS G12V for degradation. In certain embodiments, agents are conjugates comprising a peptide having the amino acid sequence X$^1$DYKDDEG (SEQ ID NO: 3), MDYKDDEG (SEQ ID NO: 1), ADYKDDEG (SEQ ID NO: 2), or derivatives thereof for binding to a KRAS G12V, a ligand to a E3 ubiquitin ligase, and a linker for conjugating the peptide to the ligand to E3 ubiquitin ligase. In certain embodiments, agents are peptides having the amino acid sequence X$^1$DYKDDEG (SEQ ID NO: 3), MDYKDDEG (SEQ ID NO: 1), ADYKDDEG (SEQ ID NO: 2), or derivatives thereof are conjugated or fused to E3 ligase binder. In certain embodiment, the conjugates or fusions are pharmaceutical compositions for use in cancer treatment. In certain embodiments, the E3 ligase binders are ligands to the von Hippel-Lindau (VHL) and cereblon (CRBN) E3 ubiquitin ligases. In certain embodiments, the E3 ligase binders are peptide-based ligands to E3 ligases or small molecule inhibitors of E3 ligases, for example:

triazolodiazepine (JQ1), 4-(4-chlorophenyl)-2,3,9-trimethyl-6H-thieno[3,2-f][1,2,4]triazolo[4,3-a][1,4]diazepine, 4-(4-chlorophenyl)-2,3,9-trimethyl-6H-thieno[3,2-f][1,2,4]triazolo[4,3-a][1,4]diazepine-6-acetic acid 1,1-dimethylethyl ester, (2S,4R)-1-((S)-2-acetamido-3,3-dimethylbutanoyl)-4-hydroxy-N-(2-hydroxy-4-(4-methylthiazol-5-yl)benzyl) pyrrolidine-2-carboxamide, (2S,4R)-1-((S)-2-(1-fluorocyclopropane-1-carboxamido)-3,3-dimethylbutanoyl)-4-hydroxy-N-(2-hydroxy-4-(4-methylthiazol-5-yl)benzyl) pyrrolidine-2-carboxamide, thalidomide, 2-(2,6-dioxopiperidin-3-yl) isoindoline-1,3-dione, pomalidomide, 4-amino-2-(2,6-dioxopiperidin-3-yl) isoindoline-1,3-dione, and 2-[[2-(2,6-dioxo-3-piperidinyl)-2,3-dihydro-1,3-dioxo-1H-isoindol-4-yl]oxy]acetic acid or salts thereof.

In certain embodiment, this disclosure relates to methods of treating cancer comprising administering an effective amount of a conjugate or fusion peptide comprising X$^1$DYKDDEG (SEQ ID NO: 3), MDYKDDEG (SEQ ID NO: 1), ADYKDDEG (SEQ ID NO: 2), or derivatives thereof conjugated or fused to E3 ligase binder to a subject in need thereof. In certain embodiments, the conjugate or fusion has a N-terminus consisting of an amino acid sequence X$^1$DYKDDEG (SEQ ID NO: 3), MDYKDDEG (SEQ ID NO: 1), ADYKDDEG (SEQ ID NO: 2) or derivative. In certain embodiments, the conjugate of fusion has a C-terminus consisting of an amino acid sequence X$^1$DYKDDEG (SEQ ID NO: 3), MDYKDDEG (SEQ ID NO: 1), ADYKDDEG (SEQ ID NO: 2) or derivative.

Combination Therapies and Kits

The present disclosure also provides methods for implementing combination therapies in which an agent known to modulate other pathways, or other components of the same pathway, or even overlapping sets of target enzymes are used in combination with an agent of the present disclosure, or a pharmaceutically acceptable salt thereof. In one aspect, such therapy includes but is not limited to the combination of one or more agents of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of checkpoint inhibitors, mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Also included as suitable chemotherapeutic cell conditioners are anti-hormonal agents that act to regulate or inhibit hormone action on tumors such as anti-estrogens including for example tamoxifen and raloxifene This disclosure further relates to a method for using the agents or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Additional pharmaceutically active compounds/agents that can be used in the treatment of cancers and that can be used in combination with one or more compound of the present invention include: epoetin alfa; darbepoetin alfa; panitumumab; pegfilgrastim palifermin; filgrastim; denosumab; AMG 102; AMG 386; AMG 479; AMG 510, AMG 655; AMG 745; AMG 951; and AMG 706, or a pharmaceutically acceptable salt thereof.

In certain embodiments, a pharmaceutical composition provided herein is administered in combination with a steroid. Suitable steroids may include, but are not limited to, 21-acetoxypregnenolone, alclometasone, amcinonide, beclomethasone, betamethasone, budesonide, chlorprednisone, clobetasol, clocortolone, cloprednol, corticosterone, cortisone, deflazacort, desonide, desoximetasone, dexamethasone, diflorasone, diflucortolone, flumethasone, flunisolide, fluocinolone acetonide, fluocinonide, fluocortolone, fluorometholone, fluprednidene acetate, fluticasone propionate, halcinonide, halobetasol propionate, hydrocortisone, loteprednol etabonate, medrysone, methylprednisolone, mometasone furoate, paramethasone, prednicarbate, prednisolone, prednisolone 25-diethylaminoacetate, prednisolone sodium phosphate, prednisone, prednylidene, tixocortol, triamcinolone, triamcinolone acetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

As one aspect of the present disclosure contemplates treatment with a combination of pharmaceutically active compounds that may be administered separately, the disclosure further relates to combining separate pharmaceutical compositions in kit form. The kit comprises two separate pharmaceutical compositions: an agent of the present disclosure, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Pharmaceutical Compositions

Also provided herein are pharmaceutical compositions that includes agents as disclosed herein, together with a pharmaceutically acceptable excipient, such as, for example, a diluent or carrier. Agents and pharmaceutical compositions suitable for use in the present disclosure include those wherein the agent can be administered in an effective amount to achieve its intended purpose.

Suitable pharmaceutical formulations can be determined by the skilled artisan depending on the route of administration and the desired dosage. See, e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body weight, body surface areas or organ size.

Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable excipients" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated.

The agents can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like.

For oral administration, suitable compositions can be formulated readily by combining a agent disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. For administration in liquid form, the composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In certain embodiments, the form must be sterile and must be fluid, e.g., can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous.

The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active agemt in the required amount in the appropriate solvent with various of the other ingredients enumerated above, as required, followed by filtered sterilization.

For administration by inhalation, agents of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The amount of agent administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures.

KRAS Mutant Protein-Protein Interaction Targets and Inhibitors

This disclosure relates to a discovery that there is molecular interaction between a mutated, activated KRAS (KRAS G12V) and an immune response mediator, JAK1 indicating that KRAS G12V drives tumorigenesis in part through suppressing the JAK1-mediated immune response pathway. Experiments indicate that KRAS G12V induces an immunosuppressive phenotype, and the disruption of the KRAS G12V-JAK1 interaction by an antagonistic peptide (designated as RasKi) can reverse such an immune escape, leading to enhanced, immune cell-mediated killing of KRAS G12V-carrying cancer cells. Thus, the KRAS G12V-JAK1 interaction represents molecular target for therapeutic discovery and development.

RasKi is a cell permeable peptide that can specifically disrupt the KRAS G12V-JAK1 interaction and induce immune cell-triggered killing of cancer cells with KRAS G12V. RasKi and derivatives can be used as anticancer immune therapeutic agents for cancers in patients with the KRAS G12V mutation, such as those found in lung, pancreatic, thyroid, and colon cancers.

Inhibitors of the KRAS G12V-JAK1 interaction are contemplates to treat patients with KRAS G12V-carrying tumors to reverse resistance to immune attacks. Although it is not intended that certain embodiments of this disclosure be limited by any particular mechanism, it is contemplated that these inhibitory agents inhibit the growth of oncogenic mutation KRAS G12V-driven tumors by re-activating the immune response pathway for enhanced immune attack. RasKi is capable of binding to KRAS-G12V allowing this peptide to be used as an imaging agent for detecting KRAS G12V mutations.

KRAS-G12V Interacts with JAK1

KRAS with a G to V mutation (G12V) was found to specifically interact with JAK1 in a panel of molecular interaction assays, including a proximity based homogenous FRET assay, GST-affinity pull-down assay, co-immunoprecipitation assay for endogenous interactions, and protein fragmentation assay (PCA) for localized interactions in live cells. JAK1 was present only in the GST-tagged KRAS-G12V protein complex rather than KRAS-WT, or other mutations, G12C and G12D through orthogonal GST pull-down assay, confirming its selectivity for G12V. This interaction could be demonstrated under native conditions. JAK1 was detected in immuno-complex with KRAS-G12V at endogenous level, but not with KRAS WT or IgG control. Similarly, KRAS-G12V was co-immunoprecipitated in complex with JAK1 by anti-JAK1 antibody in a reciprocal experiment, confirming their interaction under intracellular endogenous conditions. Further evidence came from live cell based protein-protein interaction assay with the PCA approach. The co-expression of KRAS-G12V and JAK1 in live cancer cells showed that the interaction was localized to the cell membrane, with higher fluorescent signal than that of WT and other negative controls. To further validate this interaction, the binding site of JAK1 was mapped to its pseudokinase domain for KRAS-G12V. With purified fragment of JAK1 with the pseudokinase domain and purified KRAS-G12V protein available, it was possible to test for their interaction in vitro in a defined, reconstituted system. Indeed, a biosensor assay with the Bio-Layer Interferometry (BLI) showed significant binding signal between these two purified proteins, supporting a direct interaction between KRAS-G12V and JAK1. All of these experimental results indicate that JAK1 and KRAS-G12V can interact under physiological conditions. JAK1 preferentially interacts with the mutant KRAS-G12V over the WT KRAS.

Sequences of JAK1 that Show Positive Interactions with KRASG12V

```
PK 545-855 (311 amino acids (AA)):
                                    (SEQ ID NO: 11)
QPKPREISNLLVATKKAQEWQPVYPMSQLSFDRILKKDLVQGEHLGRGTR

THIYSGTLMDYKDDEGTSEEKKIKVILKVLDPSHRDISLAFFEAASMMRQ

VSHKHIVYLYGVCVRDVENIMVEEFVEGGPLDLFMHRKSDVLTTPWKFKV

AKQLASALSYLEDKDLVHGNVCTKNLLLAREGIDSECGPFIKLSDPGIPI

TVLSRQECIERIPWIAPECVEDSKNLSVAADKWSFGTTLWEICYNGEIPL

KDKTLIEKERFYESRCRPVTPSCKELADLMTRCMNYDPNQRPFFRAIMRD

INKLEEQNPDI

N-545-672 (128 AA):
                                    (SEQ ID NO: 10)
QPKPREISNLLVATKKAQEWQPVYPMSQLSFDRILKKDLVQGEHLGRGTR

THIYSGTLMDYKDDEGTSEEKKIKVILKVLDPSHRDISLAFFEAASMMRQ

VSHKHIVYLYGVCVRDVENIMVEEFVEG

N1 545-627 (83 AA):
                                    (SEQ ID NO: 9)
QPKPREISNLLVATKKAQEWQPVYPMSQLSFDRILKKDLVQGEHLGRGTR

THIYSGTLMDYKDDEGTSEEKKIKVILKVLDPS

T4 603-627 (25 AA):
                                    (SEQ ID NO: 8)
MDYKDDEGTSEEKKIKVILKVLDPS

T4a 603-618 (16 AA):
                                    (SEQ ID NO: 4)
MDYKDDEGTSEEKKIK

RasKi: 8-mer 603-610 (8 AA):
                                    (SEQ ID NO: 1)
MDYKDDEG
```

KRAS-G12V Binds to an 8 Amino Acid Peptide (RasKi) in the Pseudokinase Domain of JAK1.

In order to better understand the molecular basis of the KRAS-G12V/JAK1 interaction, the KRAS-G12V-binding site was mapped to determine which structural elements in JAK1 might be important. After a series of truncation studies guided by structural analysis, down the binding site was narrowed to an 8 amino acid peptide in the JAK1 pseudokinase domain. This sequence of JAK1, MDYKDDEG (SEQ ID NO: 1), is poorly conserved among three JAK isoforms, supporting the specificity of KRAS-G12V for JAK1 (FIG. 2A). Interestingly, a critical reside Lys606 was identified within this 8-mer sequence as being critical binding. A charge reversal mutant of the 8-mer at this residue, K606E, significantly decreased its ability to disrupt the interaction of KRAS-G12V with JAK1 (FIG. 2D-E). Also, this single mutation in the larger fragment of the pseudokinase domain of JAK1 could attenuate its interaction with KRAS-G12V (FIG. 2G). In support of the role of the 8-mer peptide for the defined interaction, the 8-mer peptide could effectively disrupt the JAK1/KRAS-G12V interaction, either in homogenous TR-FRET assay (FIG. 2B) or in an affinity-based GST pull-down assay (FIG. 2C) with an apparent IC50 of 0.87 μM. Importantly, the disruption effect was also dependent on the intact Lys606, because the 8-mer peptide with K606E showed much decreased disruption effect (FIG. 2D). Thus, this 8-mer/K606E offers an ideal control for the 8-mer peptide for functional studies. Consistent with its importance, unlike the 8-mer WT sequence, the 8-mer/K606E peptide was incapable of competing with JAK1-FL for binding to KRAS-G12V (FIG. 2E). At endogenous level, the 8-mer could effectively disrupt the interaction, but K606E showed much lower potency (FIG. 2F). Together these lines of evidence indicate that the 8-mer of the JAK1 protein is sufficient for KRAS-G12V binding and this peptide is cell permeable and capable of disrupting the JAK1/KRAS-G12V interaction in cells. This 8-mer KRAS-G12V binding peptide with inhibitory function was named "RasKi."

RasKi, an 8-Mer Peptide, Disrupts KRAS-G12V-JAK1 Interaction, Re-Activating Immune Response It is well accepted that JAK-STAT-signaling cascade can be activated by IFNs, including type I (IFNα and IFNβ) and type II (IFNγ) IFNs. The immunomodulatory activity of IFNγ has long been appreciated, and its roles in the control of host immune response are well established. To determine whether KRAS-G12V regulate IFNγ-JAK1-STAT-dependent immune response signaling, a series of experiments were performed in overexpressed HEK293T cells and isogenic cell lines with endogenous KRAS.

Oncogenic mutations like KRAS-G12V exhibit immune suppressive phenotype. Indeed, cells with KRAS-G12V showed suppressed JAK-immune response signaling as measured (i) reduced transcriptional activity of STAT1, (ii) reduced phosphorylation of STAT1 and STAT3, and (iii) reduced expression of STAT1/3 gene products like IRF1, TAP1 and PD-L1, upon stimulation by IFNγ in comparison to KRAS-WT. It is possible that the reduced immune response in KRAS-G12V-carrying cells could be due to the effect of the KRAS-G12V interaction with JAK1. With the basal level of immune response suppression level established for KRAS-G12V over its WT counterpart, the effect of disrupting the KRAS-G12V and JAK1 interaction were tested on IFNγ-induced immune response signaling using RasKi, an interaction antagonist. As shown in FIG. 3A, while KRAS-G12V showed basal level of STAT1 transcriptional activity in comparison to that of KRAS-WT, co-expression of RasKi completely reversed the KRAS-G12V effect, showing significantly enhanced STAT1 transcriptional activity upon IFNγ treatment (FIG. 3A).

Figure 3D:
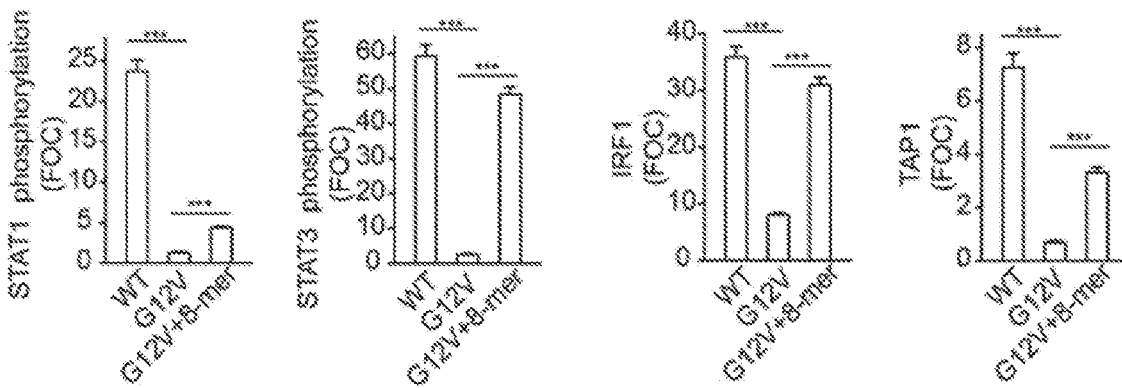
FIG. 3D shows data on the effect of KRAS-G12V and RasKi on IFN-γ stimulated pathway activation under endogenous conditions. Western Blot was performed to detect changes in the JAK-STAT pathway in SW48 cell lines (KRAS isogenic colon cancer with G12V), with or without IFN-γ (1 ng/ml) for 30 minutes. FOC bar graphs show STAT1/3 phosphorylation, IRF1 and TAP1 expression in three groups after IFN-γ stimulation comparing to basal level.
Figure 3E:
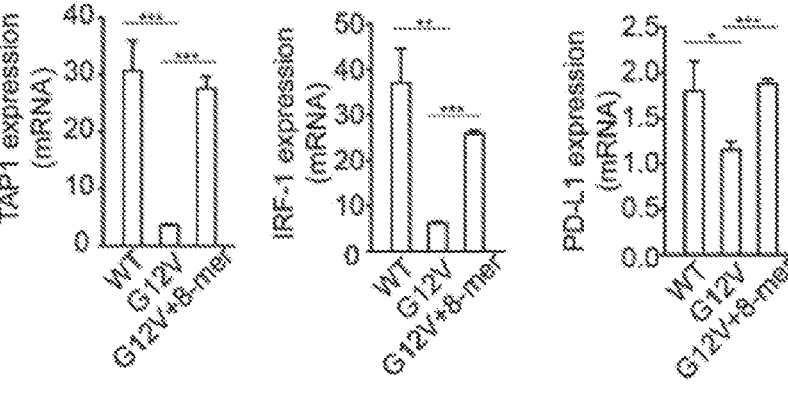
FIG. 3E shows data on the effect of KRAS-G12V and RasKi on IFN-γ stimulated mRNA expression of IFN-γ response genes under endogenous conditions. Expression of TAP1, IRF1, PD-L1 mRNA was normalized to GAPDH in SW48 cell lines as detected using RT-qPCR (reverse transcription-quantitative polymerase chain reaction). Cells were treated with IFN-γ (1 ng/ml) for 18 hours.

The RasKi effect on STAT1 and STAT3 phosphorylation and the expression of IFNγ-JAK-STAT downstream effectors IRF1, TAP1 and PD-L1 was examined. RasKi was capable of reversing the KRAS-G12V-mediated suppression of IFNγ-invoked immune signaling, as evidenced by increased STAT1/3 phosphorylation (FIG. 3B), expression of IRF1 and TAP1 proteins (FIG. 3B), and expression of mRNAs for IRF1, RAP1, and PD-L1 (FIG. 3E). Similar results were observed under endogenous conditions with the use of KRAS isogenic cell lines (FIG. 3C-E).

These results demonstrate the immune response suppressive effect of KRAS-G12V with the defined molecular biomarkers. The use of RasKi, a JAK1-KRAS-G12V interaction inhibitor, could effectively reversed the immune signaling suppression effect of KRAS-G12V, implying the critical importance of the JAK1-KRAS-G12V interaction in mediating this oncogenic driver mutation invoked immune suppression. Thus, RasKi has therapeutic potential as a KRAS-G12V-specific immune enhancer to overcome immune resistance.

RasKi, an 8-Mer Inhibitor Peptide, Enhanced Killing of G12V-Cancer Cells by IFNγ and by NK Cells In order to functionally test whether RasKi could serve as a KRAS-G12V specific immune enhancer, a series of cell viability assays were performed to examine the effect of RasKi on KRAS-G12V-mediated resistance to IFNγ-induced immuno-killing. KRAS-WT cells were more sensitive to IFNγ-induced killing than KRAS-G12V, exhibiting mutation-induced resistance. Although RasKi showed no difference without IFNγ, the treatment of cells with RasKi drastically increased IFNγ-induced killing effect in cells with KRAS-G12V in comparison to cells with KRAS-WT (FIG. 4A). This result suggests that RasKi could reverse KRAS-G12V-associated resistance to IFNγ stimulation.

Since NK cells in the immune milieu are a major cellular source of IFNγ especially during the early phase of developing immune responses, cancer cells were co-cultured together with NK cells as immune components to model the tumor microenvironment to test the RasKi function. The cell viability curves showed that RasKi per se had no effect on viability of cancer cells either with WT or G12V. However, RasKi synergized with NK92 cells to induce dose-dependent killing of cancer cells with KRAS-G12V, but not cells with WT KRAS (FIG. 4C).

To probe the mechanism by which RasKi reverses KRAS-G12V-invoked immune suppression, the involvement of the IFNγ receptor-JAK pathway in RasKi-induced killing of cells was examined with KRAS-G12V. RasKi-induced enhancement of KRAS-G12V cell killing triggered by either IFNγ, or NK92 cells, could be abolished by the treatment of cells with ruxolitinib, a JAK1 inhibitor, or an IFNγ receptor antagonist (FIGS. 4B and 4D).

RasKi8 Enhanced Killing of G12V-Cancer Cells by CD8+ T Cells

A gene-engineered CD8+ T cell was produced to specifically target an antigen expressed in an HLA-class I-restricted manner. The human leukocyte antigen (HLA) system (the major histocompatibility complex [MHC] in humans) is an important part of the immune system, which encodes cell surface molecules specialized to present antigenic peptides to the T-cell receptor (TCR) on T cells. And NY-ESO-1 is one of the most immunogenic antigens of the cancer-testis antigen (CTA) family, which are known for their ability to induce a spontaneous immune response, including both humoral and cellular immune responses. As researchers continue to search for tumor-specific antigens for the development of immune-based modalities, NY-ESO-1 is considered to be an excellent candidate for immunotherapies, because of its limited expression in normal cells, wide-ranging expression in tumors and limited off-target toxicities. Herein, engineered T cells were used with TCR specific for the tumor-associated antigen NY-ESO-1 (157-165) presented in an HLA-A*02-restricted manner. In that system, the engineered T cells would specifically identify NY-ESO-1+ HLA-A2+ cancer cells, which allow us to discover T-cell-mediated immune response in KRAS WT/G12V with the 8-mer peptide.

Firstly, H1299 cells were used to test whether this NY-ESO-1+ HLA-A2+ TCR T-cell system. H1299 cells are NY-ESO-1 positive, so HLA-A2 were transduced into H1299 cells as HLA-A2 positive group, and co-cultured with engineered T cells. The cell viability result showed that cells died much more in H1299 HLA-A2$^{+ \ cells \ comparing \ to}$ $_H$1299 HLA-A2$^-$ cells, which indicated the NY-ESO-1 T cells specific identify HLA-A2$^+$ cancer cells. To further test whether this system works in KRAS cell lines, which are all NY-ESO-1 negative, SW48 colon cancer cells were tested as an example. KRAS cell lines were transduced with an HLA-A2 lentivirus as HLA-A2+ group, and NY-ESO-1 peptide was added as NY-ESO-1+ treatment. The cell viability bar graph showed that the engineered T cells could kill more NY-ESO-1+ HLA-A2+ SW48 cancer cells, comparing to NY-ESO-1-HLA-A2-, NY-ESO-1-HLA-A2+ or NY-ESO-1+ HLA-A2-cells.

Based on the NY-ESO-1+ HLA-A2+ TCR T-cell system, the response of KRAS WT/G12V cell lines was tested with 8-mer peptide to T-cell killing effect. Cell lines were transduced with HLA-A2 lentivirus and NY-ESO-1 peptide was added directly into the cells, co-cultured with the engineered T-cells. The cell viability assay showed that WT cells are more sensitive to T-cell killing effect, however G12V cells are resistant. The 8-mer itself was tested to determine the effect in that system. The 8-mer enhanced T-cell killing in G12V cells under T-cell stimulation. K606E did not enhance T-cell killing in G12V. However, the enhancement effect of 8-mer in T-cell killing in G12V could be abolished by JAK1 inhibitor or IFNγ receptor antagonist. Similar results were observed in different KRAS isogenic colon cancer cell lines, including SW48, LIM1215 and H838, and also in patient derived KRAS WT/G12V colon cancer cells (FIG. 5A-5F).

The invention claimed is:

1. A method of treating a cancer with a KRAS G12V mutation comprising administering an effective amount of a peptide consisting of the amino acid sequence MDYKD-DEG (SEQ ID NO: 1) or ADYKDDEG (SEQ ID NO: 2) to a subject in need thereof.

2. The method of claim 1, wherein the peptide is administered in combination with another chemotherapy agent.

3. The method of claim 2, wherein the chemotherapy agent is an immune checkpoint inhibitor.

4. The method of claim 3, wherein the immune checkpoint inhibitor is ipilimumab, nivolumab, pembrolizumab, cemiplimab, atezolizumab, durvalumab, avelumab, or combinations thereof.

5. The method of claim 1, wherein the peptide is conjugated to a E3 ubiquitin ligase binder.

6. The method of claim 1, wherein the cancer is colon cancer.

7. The method of claim 1, wherein the cancer is lung cancer.

8. The method of claim 1, wherein the cancer is pancreatic cancer.

9. The method of claim 1, wherein the cancer is thyroid cancer.

10. The method of claim 1, wherein the cancer is uterine cancer.

11. The method of claim 1, wherein the cancer is gastric cancer.

* * * * *